United States Patent [19]

Connor et al.

[11] Patent Number: 5,256,680
[45] Date of Patent: Oct. 26, 1993

[54] 3,5-DI-TERTIARY-BUTYL-4-HYDROXYPHENYL-1,3,4-THIADIAZOLES, AND OXADIAZOLES AND 3,5-DI-TERTIARY-BUTYL-4-HYDROXYPHENYL-1,2,4-THIADAZOLES, OXADIAZOLES AND TRIAZOLES AS ANTIINFLAMMATORY AGENTS

[75] Inventors: David T. Connor, Ann Arbor, Mich.; Daniel L. Flynn, Mundelein, Ill.; Catherine R. Kostlan, Saline, Mich.; Michael D. Mullican, Ypsilanti, Mich.; Gary P. Shrum; Paul C. Unangst, both of Ann Arbor, Mich.; Michael W. Wilson, Ypsilanti, Mich.

[73] Assignee: Warner-Lambert Company, Morris Plains, N.J.

[21] Appl. No.: 906,255

[22] Filed: Jun. 29, 1992

Related U.S. Application Data

[60] Division of Ser. No. 753,015, Aug. 23, 1991, Pat. No. 5,155,122, which is a continuation of Ser. No. 426,814, Oct. 30, 1989, abandoned, which is a continuation-in-part of Ser. No. 277,171, Nov. 29, 1988, abandoned.

[51] Int. Cl.$^5$ ............... C07D 271/10; C07D 27/113; A61K 31/41
[52] U.S. Cl. .................................. 514/364; 548/131; 548/132; 548/133
[58] Field of Search .................. 548/131, 132, 133; 514/364

[56] References Cited

U.S. PATENT DOCUMENTS 4,618,617 10/1986 Yamamoto .

OTHER PUBLICATIONS

Derwent Abstract No. 88-156224/23 Referring to European Application No. 269,981.
Derwent Alerting Bulletin J8-B, vol. 88, No. 21 by Kanegafuchi Kagaku Referring to Japanese Application 88024498.
Derwent Abstract No. 88-180570/26 by Eisai KK, Referring to Japanese Application No. J63119-461.
Derwent Abstract No. 88-178798/26 by Eisai KK, Referring to Japanese Application No. J63115-859.
Derwent Abstract No. 88-147234/21 Referring to U.S. Pat. No. 4,743,606.
Derwent Abstract No. 87-140934/20 Referring to Japanese Application No. J62,081,343.
Derwent Abstract No. 87-051809/08 Referring to European Application No. 211670.
Derwent Abstract No. 87-203585/29 by Yamanouchi Pharm KK, Referring to Japanese Application No. 62132871.
MISC. Derwent Abstract No. 88-178974/26 Referring to Japanese Application No. J63115-860-A.
MISC. Derwent Abstract No. 87-216873/31 Referring to Japanese Application No. J62142-162-A.
MISC. Derwent Abstract No. 82-74952E/36 Referring to U.S. Pat. No. 4,636,516.

*Primary Examiner*—Robert Gerstl
*Attorney, Agent, or Firm*—Joan Thierstein; Ronald A. Daignault

[57] ABSTRACT

The present invention is novel compounds which are 3,5-di-tertiary-butyl-4-hydroxyphenyl substituted 1,2,4- and 1,3,4-thiadiazoles and oxadiazoles, and 1,2,4-triazoles, and pharmaceutically acceptable additions and base salts thereof, pharmaceutical compositions and methods of use therefor. The invention compounds are now found to have activity as inhibitors of 5-lipoxygenase and/or cyclooxygenase providing treatment of conditions advantageously affected by such inhibition including inflammation, arthritis, pain, fever, and the like.

38 Claims, No Drawings

3,5-DI-TERTIARY-BUTYL-4-HYDROXYPHENYL-1,3,4-THIADIAZOLES, AND OXADIAZOLES AND 3,5-DI-TERTIARY-BUTYL-4-HYDROXY-PHENYL-1,2,4-THIADAZOLES, OXADIAZOLES AND TRIAZOLES AS ANTIINFLAMMATORY AGENTS

This is a divisional of U.S. application Ser. No. 753,015 filed Aug. 23, 1991, now U.S. Pat. No. 5,155,122, which is a continuation of U.S. application Ser. No. 426,814 filed Oct. 30, 1989, now abandoned, which is a continuation-in-part of U.S. application No. 277,171 filed Nov. 29, 1988, now abandoned.

BACKGROUND OF THE INVENTION

The present invention is novel compounds which are 3,5-di-tertiary-butyl-4-hydroxyphenyl substituted 1,2,4- and 1,3,4-thiadazoles and oxadiazoes, and 1,2,4-triazoles, and pharmaceutically acceptable acid addition or base salts thereof, pharmaceutical compositions and methods of use therefor. The invention compounds are now found to have activity as inhibitors of 5-lipoxygenase and/or cyclooxygenase providing treatment of conditions advantageously affected by such inhibition including inflammation, arthritis, pain, pyrrhia, and the like. Thus, the present invention is also a pharmaceutical composition or method of use therefor.

U.S. Pat. No. 4,618,617 includes a generic disclosure for 1,2,4-oxadiazole derivatives of groups which may be read to include 3,5-di-tertiary butyl-4-hydroxy phenyl substituents. However, none of the disclosure specifically shows the unexpected activity of combined ring systems of the present oxadiazole and 3,5-ditertiary-butyl-4-hydroxyphenyl groups. Similarly, J61005-072-A of Derwent Abstract No. 86-051943/08 does not recognize the advantages of the present ring combination.

3,5-di-tertiary-buty-4-hydroxyphenyl substituents are also shown on pyrrole ring-containing compounds in European Application No. 269,981 abstracted as Derwent Abstract No. 88-15622/423, showing usefulness as analgesic, antipyretic, antiinflammatory, and antipsoriatic agents, and for treating bone disorders.

A 3,5-di-tertiarybutyl-4-substituted benzylidene on a

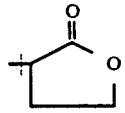

ring is disclosed for
use as antiinflammatory, analgesic, antipyretic, and antiplatelet aggregation agents in an abstract of Japanese Application 88024498 in the Derwent Alerting Bulletin J8-B, Vol. 88, No. 21 by Kanegafuchi Kagaku.

A 3,5-di-tertiarybutyl-4-hydroxybenzyl substituent for 2-pyrrolidone derivatives as antiinflammatory, analgesic, and antipyretic agents is taught by Japanese Application No. J63119-461 and J63115-859 in Derwent Abstract No. 88-180570/26 and 88-178973/26, respectively, by Eisai KK.

Other compounds disclosing either specifically or generically 3,5-di-tertiarybutyl-4-hydroxy substituents include compounds that are, for example, 3-ethenylpyridines, in U.S. Pat. No. 4,743,606 abstracted in Derwent Abstract No. 88-147234/21 and

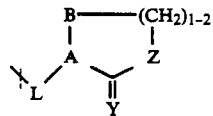

wherein L is lower alkylene, sulphur or sulphinyl; and Y is alkoxyimino, or oxo; A—B— is CH—CH$_2$— or C=CH—; and Z is lower alkylene or sulphur; in Japanese Application No. J62,081,343 in Derwent Abstract 87-140934/20.

Also, thiazolidinone derivatives are shown in European Application No. 211670 by Eli Lilly and Co. of Derwent Abstract No. 87-051809/08 and thiazole derivatives in Japanese Application No. 62132871 by Yamanouchi Pharm KK discussed in Derwent Abstract No. 87-203585/29. In the Lilly disclosure the ring systems were linked by a saturated carbon group.

Thus, the differences between the present invention and the teachings of the references are readily apparent.

SUMMARY OF THE INVENTION

The present invention is a compound of the formula (I)

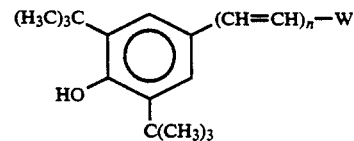

and a pharmaceutically acceptable acid addition or base salt thereof and hydrates; wherein n is zero or one, and W is

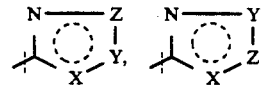

wherein X is N, NR$_1$, O, or S wherein R is hydrogen or lower alkyl;

Z is O, S, NR$_1$ or N wherein R$_1$ is independently as defined above; with the proviso that when Z is NR$_1$ or N at the same time that X is N or NR$_1$ then X must be N when Z is NR$_1$ and X must be NR$_1$ when Z is N and also with the proviso that when X is S or O then Z must be N, and that when Z is S or O then X must be N, i e. one of either X or Z must be N;

Y is (1) C—SR$_1$ wherein R$_1$ is independently as defined above, (2)

wherein R$_2$ is lower alkyl, (3)

wherein R$_2$ is as defined above, (4) C—NR$_1$R$_3$ wherein R$_1$ is independently as defined above and R$_3$ is hydrogen or lower alkyl, (5) COR₁ wherein R₁ is independently as defined above. (6) CR₄ wherein R₄ is halogen, CF₃, CO₂R₁, or

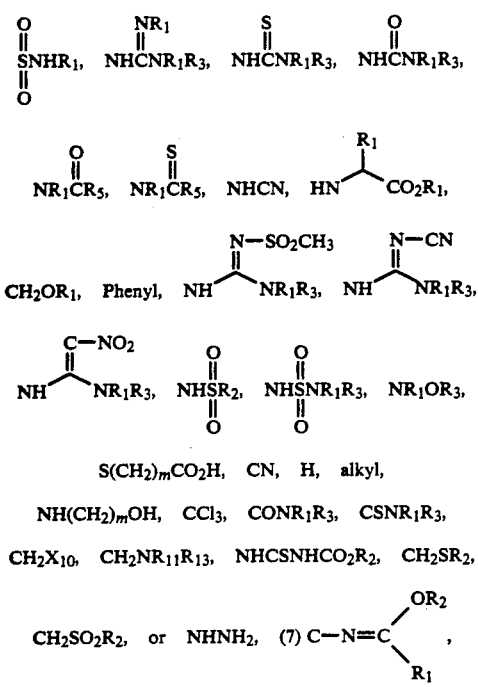

wherein m is 1, 2, or 3; $R_{11}$ and $R_{13}$ are hydrogen, lower alkyl or taken together with N form a saturated ring having from 4 to 6 carbons; $X_{10}$ is halogen or $NO_2$; $R_5$ is H, lower alkyl or $OR_1$ and $R_1$, $R_2$, and $R_3$ are independently as defined above.

The present invention is also a pharmaceutical composition for the treatment of conditions advantageously affected by the inhibition of 5-lipoxygenase and/or cyclooxygenase which comprises an amount effective for the treatment of the condition of a compound of the formula I and the pharmaceutically acceptable acid addition or base salt thereof together with a pharmaceutically acceptable carrier. The condition is meant to include, for example, arthritis or other inflammatory diseases, allergic diseases, pain, fever, and psoriasis, but preferably inflammatory diseases.

The present invention is also a method for treatment of the condition as noted above in a mammal, including humans, suffering therefrom with a compound of the formula I or the pharmaceutically acceptable acid addition or base salt thereof, in unit dosage form. The invention also provides for use of any such compound of formula I or salt thereof in the manufacture of medical therapeutic agent.

Pharmaceutical composition or use of the compound or salt of formula I is meant to include treatment understood to be prophylactic pertinent to the foregoing named condition.

The preferred compounds of the formula I in the present invention include:

5-[3,5-Bis(1,1-dimethylethyl)-4-hydroxyphenyl]-1,3,4-thiadiazole-2(3H)-thione,
5-[3,5-Bis(1,1-dimethylethyl)-4-hydroxyphenyl]-1,3,4-oxadiazol-2(3H)-one,
5-[3,5-Bis(1,1-dimethylethyl)-4-hydroxyphenyl]-1,3,4-oxadiazole-2(3H)-thione,
5-[2-[3,5-Bis(1,1-dimethylethyl)-4-hydroxyphenyl]ethenyl]-1,3,4-oxadiazole-2(3H)-one,
2,4-Dihydro-5-[2-[4-hydroxy-3,5-bis(1,1-dimethylethyl)phenyl]ethenyl]-3H-1,2,4-triazole-3-thione,
5-[3,5-Bis(1,1-dimethylethyl)-4-hydroxyphenyl]-2,4-dihydro-3H-1,2,4-triazol-3-one,
5-[3,5-Bis(1,1-dimethylethyl)-4-hydroxyphenyl]-2,4-dihydro-4-methyl-3H-1,2,4-triazol-3-one,
5-[2-[3,5-Bis(1,1-dimethylethyl)-4-hydroxyphenyl]ethenyl]-2,4-dihydro-3H-1,2,4-triazol-3-one,
5-[3,5-Bis(1,1-dimethylethyl)-4-hydroxyphenyl]-2,4-dihydro-3H-1,2,4-triazole-3-thione, and
5-[2-[3,5-Bis(1,1-dimethylethyl)-4-hydroxyphenyl]ethenyl]-1,3,4-oxadiazole-2(3H)-thione.
4-(5-amino-1,3,4-thiadiazol-2-yl)-2,6-bis(1,1-dimethylethyl)phenol,
N-[5-[3,5-bis(1,1-dimethylethyl)-4-hydroxyphenyl]-1,3,4-thiadiazol-2-yl]guanidine and the monohydrochloride salt thereof, and
5-[3,5-bis(1,1-dimethylethyl)-4-hydroxyphenyl]-1,3,4-thiadiazol-2-yl]cyanamide, and the 2-hydroxy-N,N,N-trimethylethanaminum salt thereof.

Of these the most preferred are:

5-[3,5-Bis(1,1-dimethylethyl)-4-hydroxyphenyl]-1,3,4-thiadiazole-2(3H)-thione,
4-(5-Amino-1,3,4-thiadiazol-2-yl)-2,6-bis(1,1-dimethylethyl)phenol,
N-[5-[3,5-bis[1,1-dimethylethyl)-4-hydroxyphenyl]-1,3,4-thiadiazol-2-yl]quanidine and the monohydrochloride salt thereof, and
5-[3,5-bis(1,1-dimethylethyl)-4-hydroxyphenyl]-1,3,4-thiadiazol-2-yl]cyanamide, and the 2-hydroxy-N,N,N-trimethylethanaminum salt thereof.

DETAILED DESCRIPTION OF THE INVENTION

In the compounds of formula (I) the term "lower alkyl" includes an alkyl group of from one to six carbons such as methyl, ethyl, propyl, butyl, and the like and isomers thereof. Halogen is chloro, bromo or fluoro.

The compounds I of the invention may exist as tautomers which are readily determined from art recognized tautomerism. Such tautomers are, for example, represented by formula I' and II" as follows:

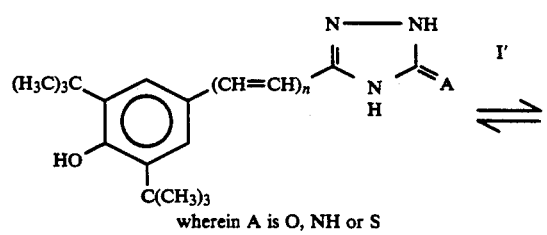

wherein A is O, NH or S

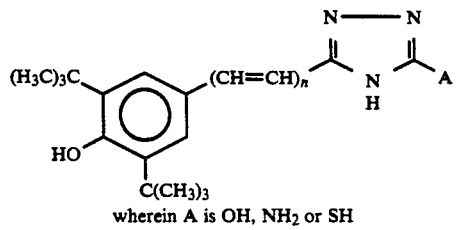

wherein A is OH, NH₂ or SH or

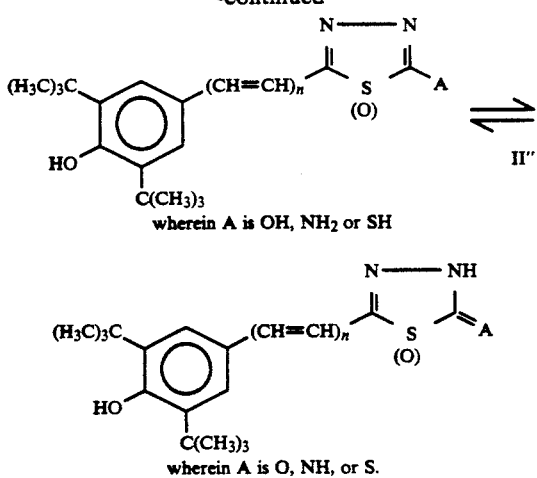

wherein A is O, NH, or S.

Appropriate compounds of formula (I) are useful in the free base form, in the form of base salts where possible, and in the form of acid addition salts. The three forms are within the scope of the invention. In practice, use of the salt form amounts to use of the base form. Pharmaceutically acceptable salts within the scope of the invention may be those derived from mineral acids such as hydrochloric acid and sulfuric acid; and organic acids such as ethanesulfonic acid, benzenesulfonic acid, p-toluenesulfonic acid, and the like, giving the hydrochloride, sulfamate, ethanesulfonate, benzenesulfonate, p-toluenesulfonate and the like, respectively, or those derived from bases such as suitable organic and inorganic bases. Examples of pharmaceutically acceptable base addition salts with compounds of the present invention include organic bases which are nontoxic and strong enough to form such salts. These organic bases form a class whose limits are readily understood by those skilled in the art. Merely for purposes of illustration, the class may be said to include mono-, di-, and trialkylamines such as methylamine, dimethylamine, and triethylamine; mono-, di-, or trihydroxyalkylamines such as mono-, di-, or triethanolamine; amino acids such as arginine and lysine; guanidine; choline N-methylglucosamine; N-methylglucamine; L-glutamine; N-methylpiperazine; morpholine; ethylenediamine; N-benzylphenethylamine; tris(hydroxymethyl)aminomethane; and the like. (See for example, "Pharmaceutical Salts," *J. Pharm. Sci.*, 66(1):1–19 (1977).) Salts of inorganic bases include sodium, potassium, calcium or the like.

The acid addition salts of said basic compounds are prepared either by dissolving the free base or acid of compound I in aqueous or aqueous alcohol solution or other suitable solvents containing the appropriate acid or base and isolating the salt by evaporating the solution, or by reacting the free base of compound I with an acid as well as reacting compound I having an acid group thereon with a base such that the reactions are in an organic solvent, in which case the salt separates directly or can be obtained by concentration of the solution. Salts can also be prepared by adding base to an aqueous alcohol solution of another salt.

The compounds of the invention may contain geometric isomers. Thus, the invention includes the individual isomers and mixtures thereof. The individual isomers may be prepared or isolated by methods known in the art.

In determining when a lipoxygenase, cyclooxygenase, or dual lipoxygenase/cyclooxygenase inhibitor is indicated, of course inter alia, the particular condition in question and its severity, as well as the age, sex, weight, and the like of the subject to be treated, must be taken into consideration and this determination is within the skill of the attendant physician.

For medical use, the amount required of a compound of formula (I) or pharmacologically acceptable salt thereof to achieve a therapeutic effect will, of course, vary both with the particular compound, the route of administration, the mammal under treatment, and the particular disorder or disease concerned. A suitable dose of a compound of formula (I) or pharmacologically acceptable salt thereof for a mammal suffering from, or likely to suffer from any condition as described hereinbefore is 0.1 μg–500 mg of the compound per kilogram body weight. In the case of systemic administration, the dose may be in the range of 0.5 to 500 mg of the compound per kilogram body weight, the most preferred dosage being 0.5 to 50 mg/kg of mammal body weight administered two or three times daily. In the case of topical administration, e.g., to the skin or eye, a suitable dose may be in the range 0.1 ng–100 μg of the compound per kilogram, typically about 0.1 μg/kg.

In the case of oral dosing for the treatment or prophylaxis of arthritis or inflammation in general, due to any course, a suitable dose of a compound of formula (I) or physiologically acceptable salt thereof, may be as specified in the preceding paragraph, but most preferably is from 1 mg to 10 mg of the compound per kilogram, the most preferred dosage being from 1 mg to 5 mg/kg of mammal body weight, for example from 1 to 2 mg/kg.

It is understood that the ordinarily skilled physician or veterinarian will readily determine and prescribe the effective amount of the compound to prevent or arrest the progress of the condition for which treatment is administered. In so proceeding, the physician or veterinarian could employ relatively low doses at first, subsequently increasing the dose until a maximum response is obtained.

While it is possible for an active ingredient to be administered alone, it is preferable to present it as a pharmaceutical formulation comprising a compound of formula (I) or a pharmacologically acceptable acid addition or base salt thereof and a pharmacologically acceptable carrier therefor. Such formulations constitute a further feature of the present invention.

The formulations, both for veterinary and for human medical use, of the present invention comprise an active ingredient in association with a pharmaceutically acceptable carrier therefor and optionally other therapeutic ingredient(s). The carrier(s) must be 'acceptable' in the sense of being compatible with the other ingredients of the formulations and not deleterious to the recipient thereof.

The formulations include those in a form suitable for oral, pulmonary, ophthalmic, rectal, parenteral (including subcutaneous, intramuscular, and intravenous), intraarticular, topical, nasal, or buccal administration. Such formulations are understood to include long-acting formulations known in the art.

The formulations may conveniently be presented in unit dosage form and may be prepared by any of the methods well-known in the art of pharmacy. All methods may include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units such as capsules, cachets, tablets, or lozenges, each containing a predetermined amount of the active ingredient; in the form of a powder or granules; in the form of a solution or a suspension in an aqueous liquid or nonaqueous liquid; or in the form of an oil-in-water emulsion or a water-in-oil emulsion. The active ingredient may also be in the form of a bolus, electuary, or paste.

The usefulness of the compounds of the present invention as inhibitors of the 5-lipoxygenase enzyme, cyclooxygenase, or in treating related diseases or conditions may be demonstrated by their effectiveness in various standard test procedures. A description of each procedure follows.

ARBL/ARBC Whole Cell 5-Lipoxygenase and Cyclooxygenase Assays

Materials

The rat basophilic leukemia cell line (RBL-1) was obtained from the American Type Culture Collection (Rockville, Md.).

Radioimmunoassay (RIA) kits of $LTB_4$ and $PGF_{2\alpha}$ were obtained from Amersham (Arlington Heights, Ill.) and Seragen (Boston, Mass.), respectively.

All tissue culture media were obtained from GIBCO (Grand Island, N.Y.).

Method

RBL-1 cells are grown in suspension culture in Eagle's minimum essential medium supplemented with 12% fetal bovine serum at 37° C. in an incubator supplied with air-5% carbon dioxide. Cells are harvested by centrifugation. They are washed with cold phosphate buffered saline pH 7.4 (PBS; NaCl, 7.1 g; $Na_2HPO_4$, 1.15 g; $KH_2PO_4$, 0.2 g; and KCl, 0.2 g/l). Cells are finally suspended PBS containing 1.0 mM calcium at a density of $2 \times 10^6$ cells/ml. Cells are incubated with and without test agent (in DMSO) (1% DMSO is without effect on arachidonic acid metabolism) for ten minutes at room temperature. Calcium ionophore A23187 (5μM) is added and cells are incubated for seven minutes at 37° C. The reaction is stopped by chilling the tubes on ice for ten minutes. Cells are separated by centrifugation and the supernatant is stored at −20°. Aliquots (100 μl) are analyzed for $LTB_4$ and $PGF_{2\alpha}$ using radioimmunoassay kits as provided by the supplier.

Table 1 contains biochemical data obtained from this whole cell assay as $IC_{50}$S which are calculated as the amount of test compound causing 50% inhibition of $LTB_4$ or $PGF_{2\alpha}$ formation.

TABLE 1

| Example | ARBL $IC_{50}{}^b$ (μM) | ARBC $IC_{50}{}^c$ (μM) |
| --- | --- | --- |
| 4 | 5.7 | 0.86 |
| 8 | 10 | 8 |
| 7 | 1.4 | 2.5 |
| 15 | 4.5 | 5.5 |

TABLE 1-continued

| Example | ARBL $IC_{50}{}^b$ (μM) | ARBC $IC_{50}{}^c$ (μM) |
| --- | --- | --- |
| 17 | 1.6 | |
| 10 | 1.4 | 0.13 |

$^b IC_{50}$ for $LTB_4$ inhibition.
$^c IC_{50}$ for $PGF_{2\alpha}$ inhibition.

Carrageenan-Induced Rat Foot Paw Edema-2 (CFE-2) Assay: Protocol

Carrageenan solution (1% w/v) is prepared by dissolving 100 mg carrageenan (Marine Colloidal Div., Springfield, N.J.) in 10 ml of sterile saline (0.9%) solution (Travenol). The solution is vortexed for 30 to 45 minutes. Animals are dosed with compound one hour before carrageenan challenge. Foot paw edema is induced by injecting 0.10 ml of the 1% carrageenan subcutaneously into the plantar portion of the right hind paw of each rat under light anesthesia. Initial foot paw volume is measured immediately following carrageenan challenge using mercury plethysmography (Buxco Electronics). Edema is measured five hours after carrageenan. The difference between the five-hour and the 1 paw volume is expressed as delta edema. The delta edema for each test group of animals is used to calculate the percent inhibition of edema achieved by the compound at the test dose compared with the vehicle control group. The $ID_{40}$ (the dose at which sweling is inhibited by 40%) is calculated by probit analysis for the dose at which 40 percent inhibition occurs.

Mycobacterium—Induced Rat Footpad Edema Assay (MFE): Protocol

Mycobacterium butyricum (5 mg/ml) is suspended in paraffin oil by sonioation for ten minutes in an ice bath. Footpad edema is induced on Day 0 by injecting 0.1 ml of the *Mycobacterium* mixture into the left hindpaw of lightly anesthetized rats. Swelling in the injected hindpaw is determined by mercury plethysmography 72 hours after injection. Groups of rats are treated with test compounds (suspended in 0.5% hydroxypropyl methylcellulose with 0.2% Tween-80) or vehicle one hour before Mycobacterium injection and on Days 1 and 2. Inhibition of swelling is determined by comparing the change in hindpaw volume in compound- and vehicle-treated rats. An $ID_{40}$ (the dose at which swelling is inhibited by 40%) is calculated by probit analysis.

Gastric Ulcerogenicity (UD): Protocol

Male outbred Wistar rats (100–250 gms) are fasted for 24 hours. After fasting, test compounds are administered orally (in 2 ml/kg of 0.5% hydroxypropyl methylcellulose) and the rats are denied access to food and water for six more hours. The rats are then sacrificed with $CO_2$ so that the stomachs can be removed, opened along the greater curvature, and evaluated for the presence of gastric ulcers. Results are expressed as the percent of rats with gastric ulcers at a given dose or as the $UD_{50}$ (the dose which causes ulcers in 50% of the rats).

The results of the CFE-2, MFE, and UD assays for each of the noted compounds are shown in the following Table 2.

TABLE 2

| Compound | In Vivo Pharmacology | | |
|---|---|---|---|
| | CFE-2[a] | MFE[b] | UD$_{50}$[c] |
| Example 4[d] | 1.9 | 3.2 | N @ 200 |

[a] ID$_{40}$ in mg/kg, PO.
[b] ID$_{40}$ in mg/kg, PO.
[c] Dose in mg/kg PO which produces a 50% occurrence of ulcers in rats. N is 0% of rats having ulcers at 200 mg.
[d] Compound tested as its sodium salt.

In addition to the compounds of formula I, the pharmaceutical compositions can also contain other active ingredients, such as cyclooxygenase inhibitors, nonsteroidal antiinflammatory drugs (NSAIDs), peripheral analgesic agents such as zomepirac, diflunisal, and the like. The weight ratio of the compound of the formula I to the second active ingredient may be varied and will depend upon the effective dose of each ingredient. Generally, an effective dose of each will be used. Thus, for example, when a compound of the formula I is combined with an NSAID, the weight ratio of the compound of the formula I to the NSAID will generally range from about 1000:1 to about 1:1000, preferably about 200:1 to about 1:200. Combinations of a compound of the formula I and other active ingredients will generally also be within the aforementioned range, but in each case, an effective dose of each active ingredient should be used.

Combinations of a compound of the formula I and other active ingredients will generally be in the aforementioned ratios.

NSAIDs can be characterized into five groups:
(1) the propionic acid derivatives;
(2) the acetic acid derivatives;
(3) the fenamic acid derivatives;
(4) the biphenylcarboxyic acid derivatives; and
(5) the oxicams or a pharmaceutically acceptable salt thereof.

The propionic acid derivatives which may be used comprise: ibuprofen, ibuprofen aluminum, indoprofen, ketoprofen, naproxen, benoxaprofen, flurbiprofen, fenoprofen, fenbufen, pirprofen, carprofen, oxaprozin, pranoprofen, miroprofen, tioxaprofen, suprofen, alminoprofen, tiaprofen, fluprofen, and bucloxic acid. Structurally related propionic acid derivatives having similar analgesic and antiinflammatory properties are also intended to be included in this group.

Thus, "propionic acid derivatives" as defined herein are nonnarcotic analgesics/nonsteroidal antiinflammatory drugs having a free —CH(CH$_3$)COOH or —CH$_2$CH$_2$COOH group (which optionally can be in the form of a pharmaceutically acceptable salt group, e.g., —CH(CH$_3$)COO$^-$NA$^+$ or —CH$_2$CH$_2$COO$^-$Na$^+$), typically attached directly or via a carbonyl function to a ring system, preferably to an aromatic ring system.

The acetic acid derivatives which may be used comprise: indomethacin, which is a preferred NSAID, sulindac, tolmetin, zomepirac, diclofenac, fenclofenac, alclofenac, ibufenac, isoxepac, furofenac, tiopinac, zidometacin, acemetacin, fentiazac, clidanac, oxpinac, and fenclozic acid. Structurally related acetic acid derivatives having similar analgesic and antiinflammatory properties are also intended to be encompassed by this group.

Thus, "acetic acid derivatives" as defined herein are nonnarcotic analgesics/nonsteroidal antiinflammatory drugs having a free —CH$_2$COOH group (which optionally can be in the form of a pharmaceutically acceptable salt group, e.g. —CH$_2$COO$^-$Na$^+$), typically attached directly to a ring system, preferably to an aromatic or heteroaromatic ring system.

The fenamic acid derivatives which may be used comprise: mefanamic acid, meclofenamic acid, flufenamic acid, niflumic acid, and tolfenamic acid. Structurally related fenamic acid derivatives having similar analgesic and antiinflammatory properties are also intended to be encompassed by this group.

Thus, "fenamic acid derivatives" as defined herein are nonnarcotic analgesics/nonsteroidal antiinflammatory drugs which contain the basic structure:

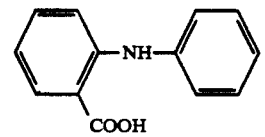

which can bear a variety of substituents and in which the free —COOH group can be in the form of a pharmaceutically acceptable salt group, e.g., —COO$^-$Na$^+$.

The biphenylcarboxylic acid derivatives which can be used comprise: diflunisal and flufenisal. Structurally related biphenylcarboxylic acid derivatives having similar analgesic and antiinflammatory properties are also intended to be encompassed by this group.

Thus, "biphenylcarboxylic acid derivatives" as defined herein are nonnarcotic analgesics/nonsteroidal antiinflammatory drugs which contain the basic structure:

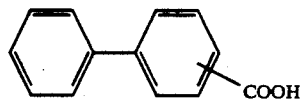

which can bear a variety of substituents and in which the free —COOH group can be in the form of a pharmaceutically acceptable salt group, e.g., —COO—Na$^+$.

The oxicams which can be used in the present invention comprise: piroxicam, sudoxicam, isoxicam, and 4-hydroxyl-1,2-benzothiazine 1,1-dioxide 4-(N-phenyl)-carboxamide. Structurally related oxicams having similar analgesic and antiinflammatory properties are also intended to be encompassed by this group.

Thus, "oxicams" as defined herein are nonnarcotic analgesics/nonsteroidal antiinflammatory drugs which have the general formula:

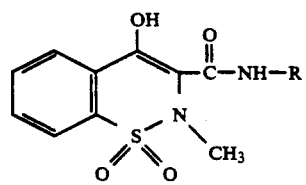

wherein R is an aryl or heteroaryl ring system.

The following NSAIDs may also be used: acemetacin, alminoprofen, amfenac sodium, aminoprofen, anitrazafen, antrafenine, auranofin, bendazac lysinate, benzydamine, beprozin, broperamole, bufezolac, carprofen, cinmetacin, ciproquazone, clidanac, cloximate, dazidamine, deboxamet, delmetacin, detomidine, dexindoprofen, diacerein, di-fisalamine, difenpyramide, emorfazone, enfenamic acid, enolicam, epirizole, etersalate, etodolac, etofenamate, fanetizole mesylate, fenclofenac, fenclorac, fendosal, fenflumizole, fentiazac, feprazone, floctafenine, flunixin, flunoxaprofen, fluproquazone, fopirtoline, fosfosal, furcloprofen, furofenac, glucametacin, guaimesal, ibuproxam, isofezolac, isonixim, isoprofen, isoxepac, isoxicam, lefetamine HCl, leflunomide, lofemizole, lonazolac calcium, lotifazole, loxoprofen, lysin, clonixinate, meclofenamate sodium, meseclazone, microprofen, nabumetone, nictindole, nimesulide, orpanoxin, oxametacin, oxapadol, oxaprozin, perisoxal citrate, pimeprofen, pimetacin, piproxen, pirazolac, pirfenidone, pirprofen, pranoprofen, proglumetacin maleate, proquazone, pyridoxiprofen, sudoxicam, suprofen, talmetacin, talniflumate, tenoxicam, thiazolinobutazone, thielavin B, tiaprofenic acid, tiaramide HCl, tiflamizole, timegadine, tioxaprofen, tolfenamic acid, tolpadol, tryptamid, ufenamate, and zidometacin.

Finally, NSAIDs which may also be used include the salicylates, specifically aspirin, and the phenylbutazones, and pharmaceutically acceptable salts thereof.

Pharmaceutical compositions comprising the formula I compounds may also contain as the second active ingredient, antihistamine agents such as benadryl, dramamine, histadyl, phenergan, and the like. Alternatively, they may include prostaglandin antagonists such as those disclosed in European Patent Application 11,067 or thromboxane antagonists such as those disclosed in U.S. Pat. No. 4,237,160. They may also contain histidine decarboxylase inhibitors such as α-fluoromethylhistidine, described in U.S. Pat. No. 4,325,961. The compounds of the formula I may also be advantageously combined with an $H_1$ or $H_2$-receptor antagonist, such as for instance cimetidine, ranitidine, terfenadine, famotidine, temelastine, acrivastine, loratadine, cetrizine, tazifylline, azelastine, aminothiadiazoles disclosed in EP 81102976.8 and like compounds, such as those disclosed in U.S. Pat. Nos. 4,283,408; 4,362,736; 4,394,508, and European Patent Application No. 40,696. The pharmaceutical compositions may also contain a $K^+/H^+$ ATPase inhibitor such as omeprazole, disclosed in U.S. Pat. No. 4,255,431, and the like. Each of the references referred to in this paragraph is hereby incorporated herein by reference.

The compounds of the formula I and their salts are prepared generally by the following processes and constitute a further aspect of the present invention.

In the following processes Ar=

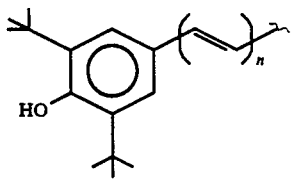

where n is 0 or 1.

Under certain circumstances as discussed below, it is necessary to protect the phenolic OH of Ar in various intermediates to give QAr where QAr is

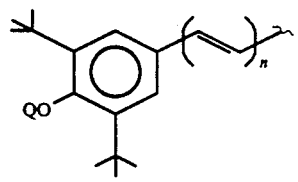

where Q is a suitable oxygen protecting group, preferably methoxyethoxymethyl (MEM) and where n=0 or 1.

The MEM group is removed later using 1) Lewis acids such as $ZnBr_2$ in halogenated solvents such as methylene chloride, chloroform, and dichloroethane at 0° to 60° C., 2) mineral acids such as HCl, HBr, or $HNO_3$ in solvents such as water, alkanols, tetrahydrofuran, dialkylethers, dioxane, glyme, diglyme at 0° to 60° C. or 3) organic acids such as acetic acid in the solvents described in 1) and 2) at 0° to 60° C.

Introduction and removal of such suitable oxygen protecting groups are well-known in the art of organic chemistry; see for example "Protective Groups in Organic Chemistry," J. F. W. McOmie, ed., (New York, 1973), pages 43ff, 95ff, J .F .W. McOmie, *Advances in Organic Chemistry*, Vol. 3, 159-190 (1963); J. F. W. McOmie, *Chem. & Ind.*, 603 (1979), and T. W. Greene, "Protective Groups in Organic Synthesis", Wiley (New York) 1981, Chapters 2, 3, and 7.

Examples of suitable oxygen protecting groups are benzyl, trialkylsilyl, ethoxyethyl, methoxyethoxymethyl, methoxymethyl, trialkylsilylethyl, and the like.

In the process described herein for the preparation of compounds of this invention the requirements for protective groups are generally well recognized by one skilled in the art of organic chemistry, and accordingly the use of appropriate protecting groups is necessarily implied by the processes of the charts herein, although such groups may not be expressly illustrated.

The method of preparation for compounds 7, 8, and 9 in Scheme 1 from compound 1, where n=0, are illustrated below. The phenolic OH of the known nitrile 1 is protected to give 2 using Q halogen, preferably MEMCl, in the presence of bases such as trialkylamines and alkalihydrides in ether solvents such as diethyl ether, diisopropylether, t-butylmethylether, tetrahydrofuran, dioxane, glyme or diglyme; or chlorinated solvents such as dichloromethane, chloroform, dichloroethane, or carbon tetrachloride; or aromatic solvents such as benzene, toluene, xylene, mesitylene or chlorinated benzenes at −10° to 200° C. for up to five days. Compound 2 is treated with $NaNHNH_2$, $LiNHNH_2$ or $KNHNH_2$ to give amidrazone 3 in ether solvents at 0° to 60° C. The reaction of amidrazone 3 with 1,1-carbonyldimidazole, phosgene, diphosgene or triphosgene in the presence of trialkylamines in ether solvents or chlorinated solvents at 0° to 200° C. for up to five days gives triazolone 4. In a similar manner, compound 5 is prepared from 3 using 1,1-thiocarbonyldiimidazole or thiophosgene as reagents. Compound 6 is prepared from 3 using carbon disulfide in chlorinated or aromatic or ether solvents or alkanols at 0° to 200° C. for up to five days. Compounds 4, 5, and 6 are deprotected as described above to give 7, 8 and 9.

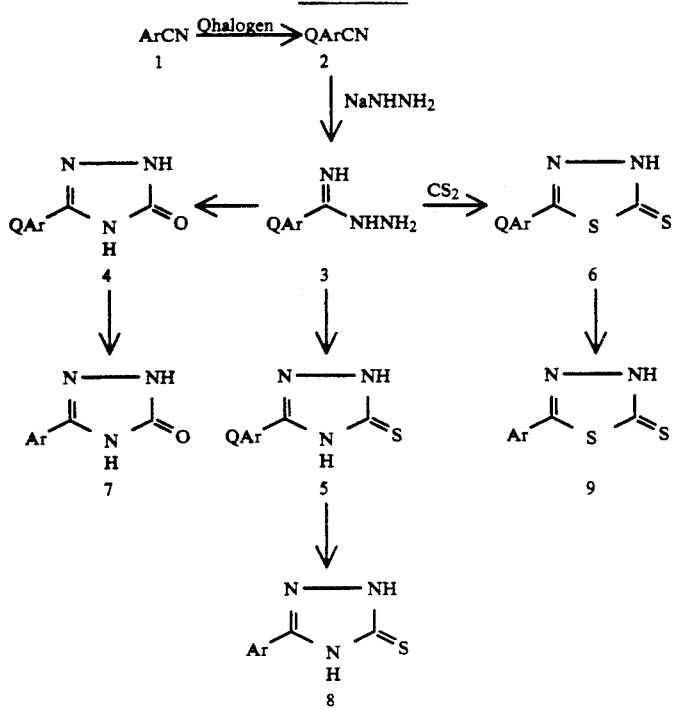

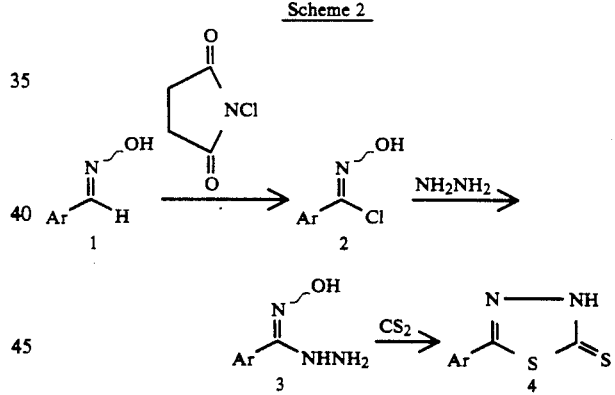

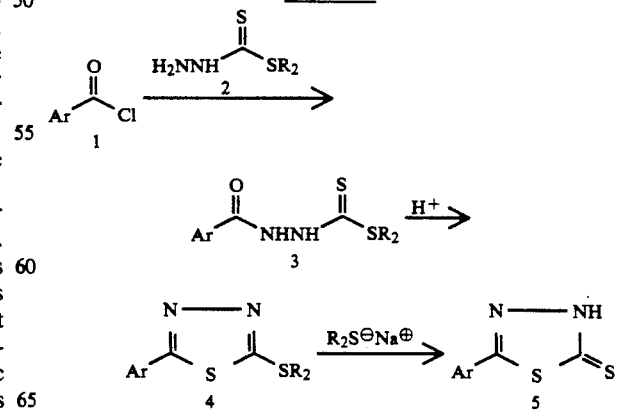

The procedures which may be used for the preparation of compounds 2 to 4 of Scheme 2 from compound 1 where n=0 or 1 are described below.

Compounds of structure 4 in Scheme 2 are prepared by treating oxime 1 with N-chlorosuccinimide in dimethylformamide (DMF) or dimethylsulfoxide (DMSO), or chlorinated or aromatic or ether solvents at 0° to 60° C. for up to five days to give 2. Compound 3 is prepared by treating 2 with hydrazine and trialkylamine, if only one equivalent of hydrazine is used, in ether solvents or alkanols at 0° to 60° C. for up to five days. Treatment of 3 with $CS_2$ in DMF or DMSO or chlorinated or aromatic or ether solvents or alkanols or neat at 0° to 60° C. for up to five days gives 4.

Compounds of structure 4 and 5 in Scheme 3 where n=0 or 1 are prepared by the following procedures.

Compound 3 is prepared from 1 using 2 in DMF or DMSO or chlorinated or ether solvents at 0° to 60° C. for up to five days. In addition, $R_2$ in compound 2 is defined as $K^+$ or $Na^+$ or $Li^+$ to give 4 where $R_2$ is transformed to H after treatment with acid. Treatment of 3 with acid, such as aryl sulfonic acids or alkylsulfonic acids or mineral acids, in chlorinated or aromatic or ether solvents at 0° to 150° C. for up to five days gives 4. Compound 5 is prepared from 4 using sodium or lithium or potassium alkythiolates, or KCN, NaCN in DMF at 0° to 150° C. for up to five days.

The following procedures for preparing compounds 6 to 11 of Scheme 4 from compound 1 of Scheme 4 where n=0 or 1 are described below. Conversion of 1 to 2 is effected using thionyl chloride or oxalyl chloride and a catalytic amount of DMF in chlorinated or ether solvents at 0° to 100° C. for up to five days. Compound 4 is prepared from 2 using 3 in chlorinated, aromatic or ether solvents at 0° to 120° C. for up to five days. Treatment of 4 with mineral acids in water and ether solvents or alkanols gives hydrazide 5. Compound 6 is prepared from 5 using alkylisothiocyanates in ether solvents or alkanols at 0° to 100° C. for up to five days followed by aqueous NaOH and refluxing the reaction mixture.

Compound 7 is prepared by reacting 5 with alkylisocyanate as described for the preparation of 6. Treatment of 5 with 1,1-carbonyldiimidazole or phosgene or diphosgene or triphosgene in chlorinated or ether solvents in the presence of trialkylamines at 0° to 100° C. for up to five days gives 8. Treatment of 5 with CS$_2$ in the presence of one equivalent of KOH in alkanols at 0° to 150° C. gives oxadiazolethione 9.

Treatment of 9 with hydrazine in water and alkanols at 0° to 150° C. for up to five days gives 11. Compound 10 is prepared from 5 using sodium isocyanate, neutralized with one equivalent of a mineral acid, in alkanols at 0° to 100° C. for up to five days.

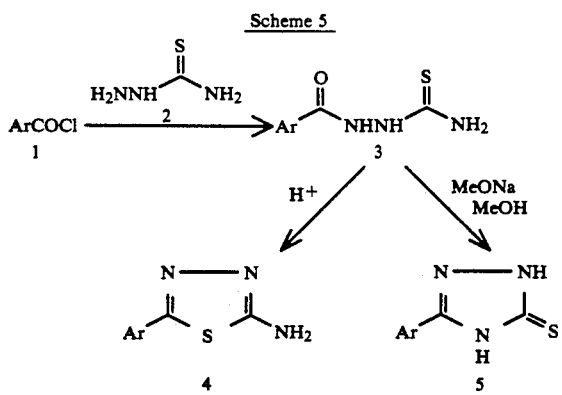

The methods for the preparation of compounds 6–13 in Scheme 6 where $X_1$ is O, S or $NR_1$ and $R_6$ is H, lower alkyl, phenyl, $CH_2Br$, $CH_2Cl$ or $CH_2NO_2$, and $R_7$ is lower alkyl, phenyl, or $CF_3$, and $R_8$ is $SO_2R_2$, CN or $SO_2aryl$, and $R_9$ is Cl, $SR_2$, $SOR_2$, $SO_2R_2$, $OR_2$ or Oaryl are described below. The conversion of 1 where n=0 or 1 to 8, 10, and 13 is effected using 3, 4, and 5, respec-

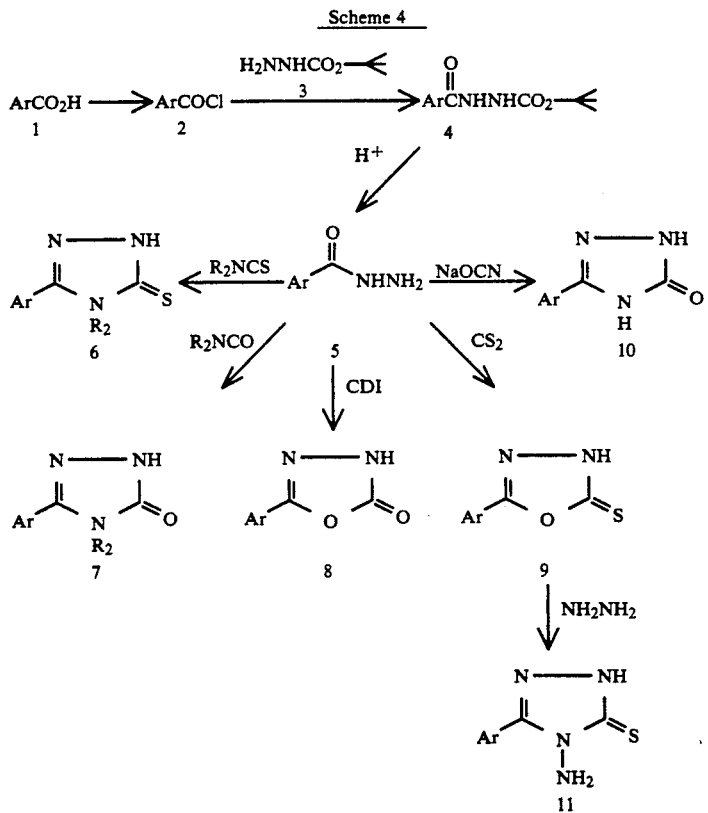

Compounds 4 and 5 of Scheme 5 are prepared from compound 1 as described below. The acid chloride 1 is converted to 3 using thiosemicarbazide 2 in ether solvents at 0° to 100° C. for up to five days. Treatment of 3 with alkyl or arylsulfonic acids in aromatic or ether solvents at 80° to 150° C. for up to five days gives 4. Compound 5 is prepared from 3 using a base such as sodium, lithium, or potassium alkoxides in alkanols at 60° to 150° C. for up to five days.

tively, in solvents such as tetrahydrofuran, diethylether, diisopropyl ether, t-butylmethylether, dioxane, benzene, toluene, acetonitrile, DMF or DMSO at 0° to 150° C. for up to five days. Treatment of 1 with 1,1-carbonyldiimidazole, phosgene, diphosgene, or triphosgene in the presence of trialkylamine in aromatic or ether solvents gives 6. Compound 11 is prepared from 10 where $X_1$ is O, S or $NR_2$ and n=0 using lithium, sodium or potassium amide 14 in ether solvents. The conversion of 8 to 9 and 11 to 12 is effected using $P_2S_5$ or Lawesson's reagent in ether solvents at 20°0 to 150° C. for up to five days.

Compound 7 is prepared from 1 using trialkylorthoesters 2 neat or in alkanols, aromatic or ether solvents in the presence of a catalytic amount of acid such as aryl or alkyl sulfonic acid or mineral acids.

The preparation of substituted 1,2,4-oxadiazoles is well known in the art (see, for example, L. B. Clapp, *Advances in Heterocyclic Chem.*, 20, 65 (1976)).

For a compound of Formula I, wherein n is zero and W is

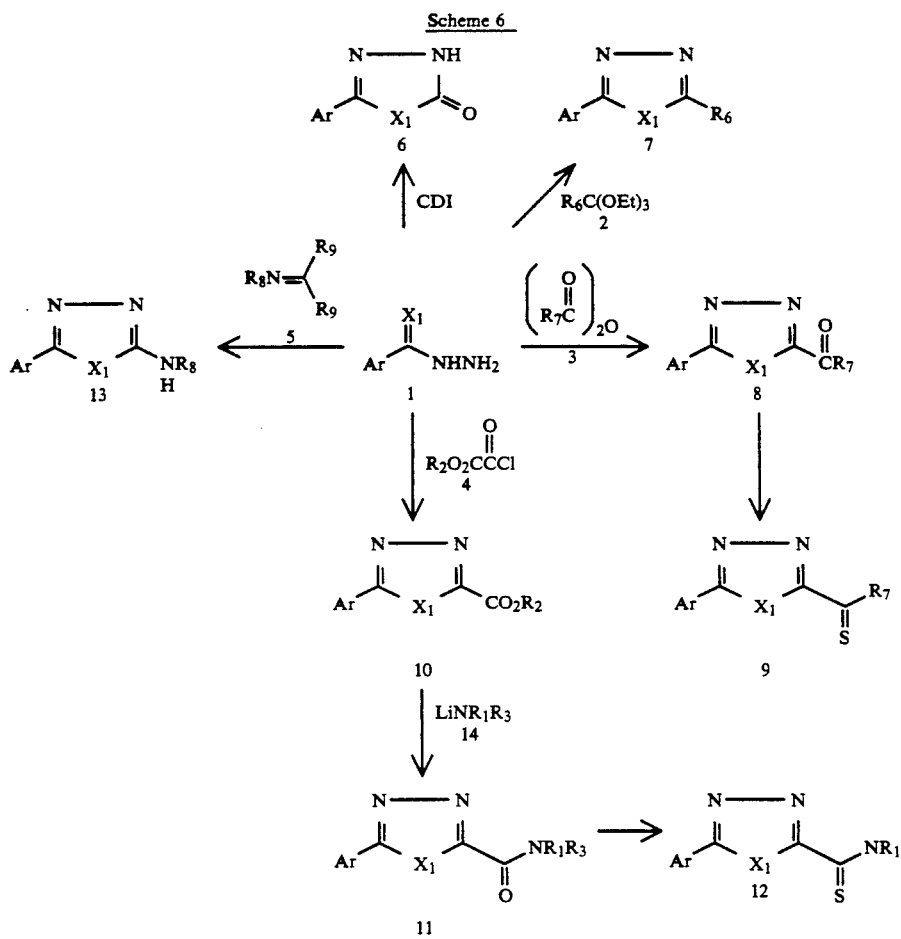

A method of preparing compound 3 from 1 in Scheme 7 where n=0 is described below. The aminoguanidine HCl, $H_2SO_4$ or $HNO_3$ salt is neutralized with a sodium, lithium or potassium alkoxide in an alkanol or ether solvent and then treated with 1. The reaction is run at 20° to 150° C. for up to five days to give 2. Deprotection of 2 using the above described conditions gives 3.

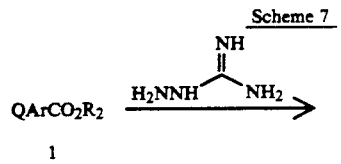

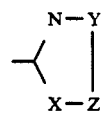

wherein X is O, Z is N,
and Y is C—$NH_2$ the procedure of K. R. Huffman and F. C. Schaefer, *J. Org. Chem.*, 28, 1812 (1963), beginning with a suitable imino ester, may be used. Other functional groups, instead of amino, are prepared by the procedures cited below.

| Y | |
|---|---|
| C—OH | F. Eloy, A. Deryckere and A. van Overstraeten, Bull. Soc. Chim. Belges, 78, 47 (1969); and O. Tsuge, S. Urano, and K. Oe, J. Org. Chem., 45, 5130 (1980). |
| C-Halogen | F. Eloy, cited above; and G. R. Humphreys and S. H. B. Wright, J. Heterocyclic Chem., 26, 23 (1989). |
| C—SH | D. S. Tarbell and D. K. Fukushima, Organic Syntheses, 27, 81 (1947). |
| C—$SR_2$ | B. W. Nash, R. A. Newberry, R. Pickles, and W. K. Warburton, J. Chem. Soc.(c), 2794 (1969). |

| Y | |
|---|---|
| C—R$_2$ | M. Yamamoto, U.S. Pat. No. 4,618,617 (1986). | wherein R$_2$ is as defined above.

For a compound of Formula I, wherein n is zero and W is

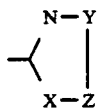

wherein X is N, Z is O,
and Y is C—NH$_2$ the procedure of F. Eloy and R. Lenaers, *Helv. Chim. Acta*, 49, 1430 (1966), involving the reaction of guanidine with a suitable carboxyimidoyl halide may be used. Other functional groups, instead of amino, are prepared by the procedures cited below.

| Y | |
|---|---|
| C—OH | A. R. Katritzky, B. Wallis, R. T. C. Brownlee, and R. D. Topson, Tetrahedron, 21, 1681 (1965). |
| C-Halogen | T. Fujita, T. Fuji, and A. Ide, Yakugaku Zasshi, 84, 1061 (1964). |
| C—SH, C—SR$_2$ | M. Selim and M. Selim, Bull. Soc. Chim. Fr., 823 (1969); and R. M. Paton and D. G. Hamilton, Tetrahedron Letters, 24, 5141 (1983). |
| C—R$_2$ | S-Chiou and H. J. Shine, J. Heterocyclic Chem., 26, 125 (1989). |

Preparative procedures for substituted 1,2,4-thiadiazoles are also well known (see, for example, F. Kurzer, *Advances in Heterocyclic Chem.*, 32, 285 (1982)).

For a compound of Formula I, wherein n is zero and W is

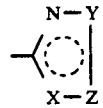

wherein X is N, Z is S,
and Y is C—Halogen, the procedure of J. Goerdeler, H. Groschopp, and U. Sommerlad, *Chem. Ber.*, 90, 182 (1957), consisting of condensing perchloromethylmercaptan with a suitable amidine, may be used. The resulting 5-halogen-substituted thiadiazole is then treated with a variety of well-known reagents to prepare analogs in which Y is C—OH, C—SR$_1$, or C—NHR$_1$, wherein R$_1$ is as defined above.

A related synthetic procedure for compounds wherein Y is C—NH$_2$ is that of J. Goerdeler, K. Wember, and G. Worsch, *Chem. Ber.*, 87, 57 (1954).

For a compound of Formula I, wherein n is zero and W is

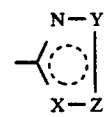

wherein X is S, Z is N,
and Y is C—NH$_2$ the procedure of C. G. Newton, W. D. Ollis, and D. E. Wright, *J. Chem. Soc. Perk. Trans. I,*
75 (1984, or B. Junge, German Patent 2,402,228 (1974), employing substituted thioamides as starting materials, may be used.

When Y is C—OH, the procedure of O. Tsuge, et al, previously cited, or that of J. Perronnet, L. Taliani, and A. Teche, U.S. Pat. No. 4,067,720 (1978), may be advantageously employed.

Additional thiadiazole analogs are prepared by diazotization of amines and other standard transformations.

Schemes 8-13 outline the functional group transformation which may be performed on Y in compounds of formula I.

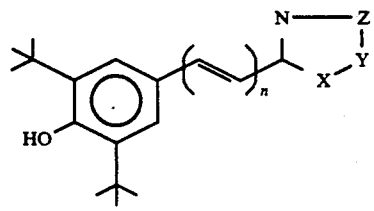

or

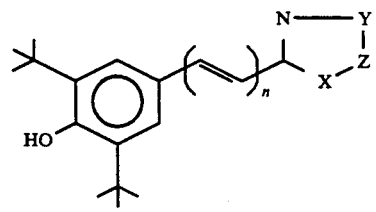

wherein n, Y, X, and Z are described above.

Under certain circumstances discussed below the phenolic OH of 1 may be protected as described above to give

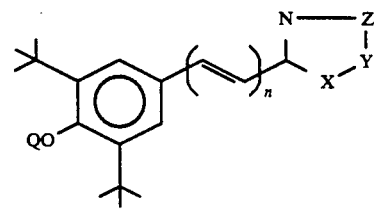

or

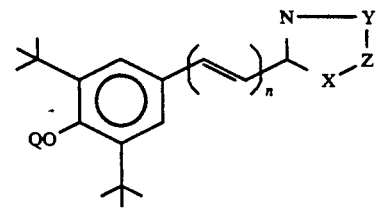

wherein Q is a protecting group as described above, and n, X, Y, and Z are described above.

Scheme 8 shows methods for the conversion of compounds of type I wherein Y is C—OH (1) to compounds of type I wherein Y is C—OAlkyl (2) by treatment of 1 with an alkyl halide in the presence of a base such as NaH, NaOH, KOH, KH, LiOH, t-BuOH or triethylamine.

Treatment of 1 with PCl$_5$, PCl$_3$, or POCl$_3$ in benzene, toluene, chloroform or methylene chloride gives a compound of type 3. Treatment of 4 under standard Sandmeyer reaction conditions also yields 3.

Scheme 8

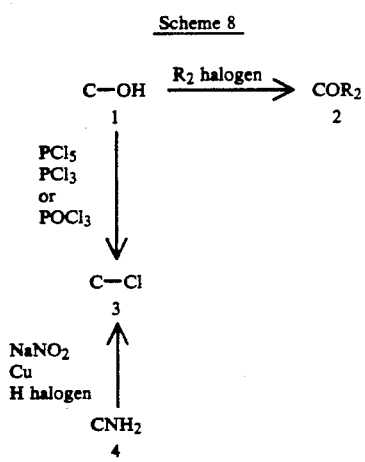

Scheme 9 shows processes for conversion of compounds of type I wherein Y is C-SH (1) to compounds 2, 3, 4, 5, 6, and 7.

Treatment of 1 with bases such as KH, NaH, or t-BuOK in the presence of an omega-halocarboxylic lower alkylester in an aprotic solvent such as diethylether, tetrahydrofuran or dimethylformamide, gives 2. Hydrolysis of 2 under standard basic conditions give the corresponding acid 4.

Treatment of 1 with alkyl halides under the conditions described above gives 3.

Treatment of 3 with excess oxidizing agents such as $KMnO_4$, $H_2O_2$ in acetic acid, or m-chloroperbenzoic acid (MCPBA) in chloroform or methylene chloride gives sulfone 5. Treatment of 3 with one equivalent of the above oxidizing agent gives sulfoxide 6.

Treatment of 1 with an oxidizing agent such as chlorine in acetic acid or sodium hyperchlorite, followed by an amine gives a sulfonamide of type 7.

Scheme 9

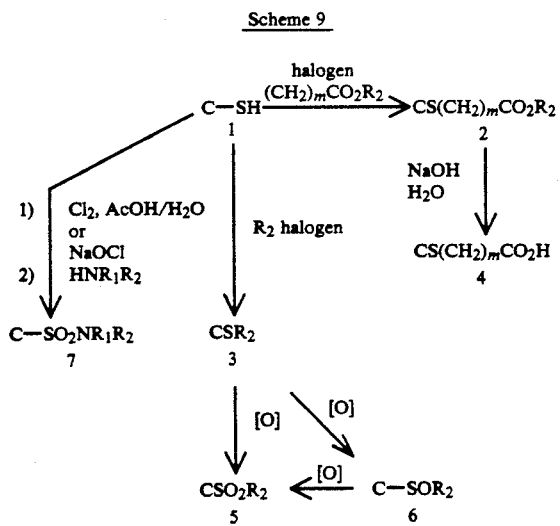

Scheme 10 shows the conversion of compounds of type I wherein Y is $C-SO_2R_2$ (1), C-Cl (2) or $C-CCl_3$ (3) to compounds 4, 5, 6, 7, 8, 9, 10, 11, 12, 13, and 14 on treatment with the nucleophiles listed in Scheme 10.

Compounds 7, 12, 13, and 14 are prepared by treating 1, 2, or 3 with the sodium or potassium salt of the respective anion in a solvent such as DMF.

Compounds 4, 5, 6, 8, 9, 10, and 11 are prepared by treating 1, 2, or 3 with the respective nucleophile in a solvent such as ethanol, isopropano, tertiary butanol, or DMF/water. Triethylamine or sodium tertiary butoxide are added in cases in which neutralization of an acid is required.

Scheme 10

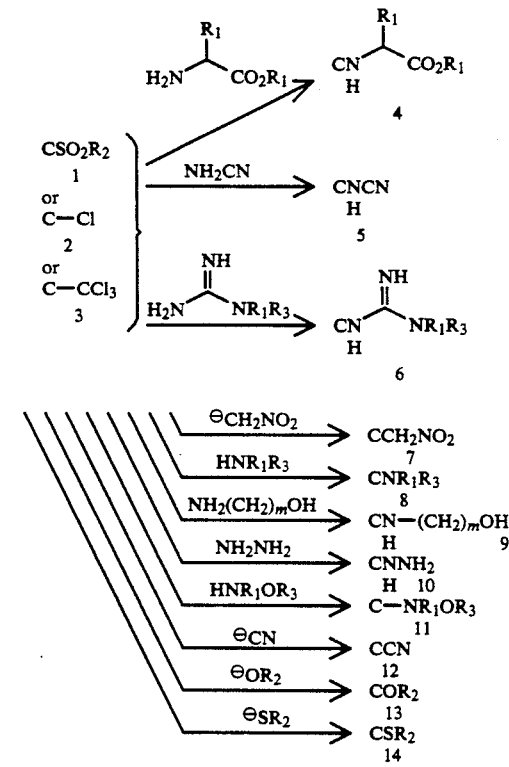

In Scheme 11 where $R_5$ is $OR_2$, $R_1$ or aryl and $R_{10}$ is Cl, $OR_2$, $SR_2$, treatment of compounds of type I wherein Y is $C-NH_2$ with isocyanates or isothiocyanates in hexane, benzene or toluene gives compounds 2, 3, 4, and 5. Treatment of 1 with sodium nitrite in sulfuric acid, followed by hydrolysis of the diazonium salt gives 7. Alkylation, acylation, or sulfonylation of 1 with various electrophiles gives compounds 6, 8, 12, and 13. Amine 8 can be further treated with other electrophiles to yield 9, 10, and 11. Amides 9 and 12 are converted to the corresponding thioamides 10 and 13 with treatment with $P_2S_5$ or Lawesson's reagent.

Scheme 11

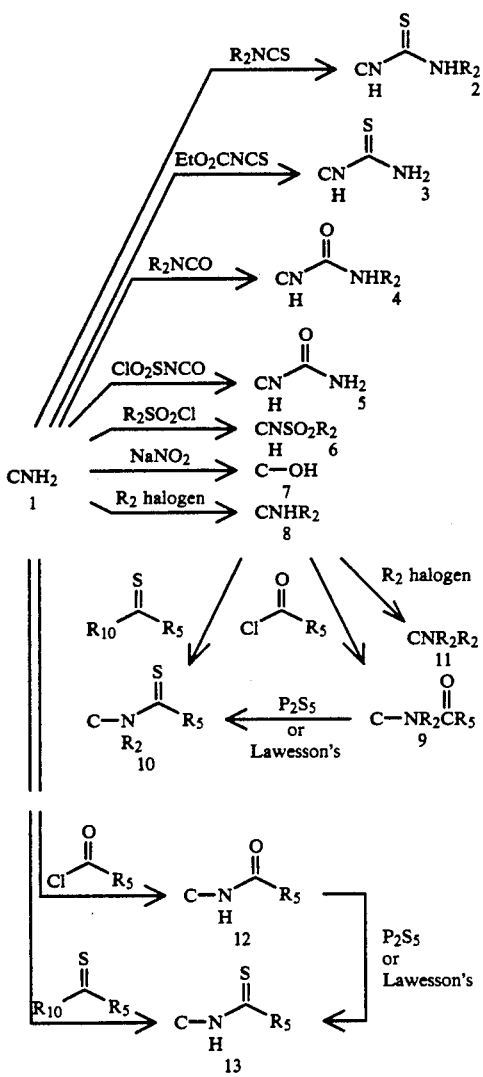

In Scheme 12, treatment of compounds of type 1 wherein Y is C-CH$_2$Cl with various nucleophiles in dimethylsulfoxide or dimethylformamide gives 2, 3, and 4. Treatment of 4 with excess oxidizing agent such as KMnO$_4$, H$_2$O$_2$ in acetic acid, or M-chloroperbenzoic acid (MCPBA) in chloroform or methylene chloride gives sulfone 5.

Scheme 12

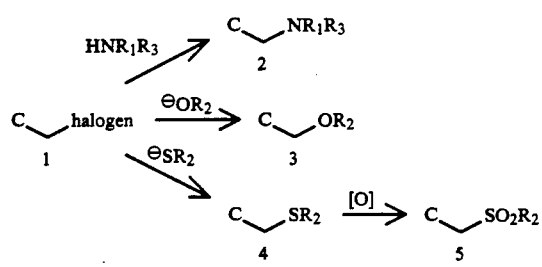

Methods for the preparation of 5, 6, and 7 in Scheme 13 are described below. Compound 1 may be converted to 5, 6, or 7 using 2, 3, or 4, respectively, in aromatic, chlorinated or ether solvents at 0° to 200° C. The base such as sodium methoxide, potassium butoxide or triethylamine may be needed to catalyze the reaction or to neutralize acid that may be produced. This step is followed by treatment of the reaction with HNR$_1$R$_3$ to give 5, 6, or 7, respectively.

Treatment of 8 in Scheme 13 with R$_2$halogen in ether solvents in the presence of a base such as sodium methoxide, potassium t-butoxide or triethylamine at 0° to 150° C. gives 9. Compounds 5, 6 or 7 may be prepared from 9 using 10, 11, or 12, respectively, in aromatic or ether solvents at 0° to 150° C. The anion of compound 10 may be generated using bases such as triethylamine, potassium t-butoxide, or sodium hydride. The reactions using 11 and 12 could employ a base such as potassium, sodium, t-butoxide, triethylamine. The phenolic OH of 1, 8, or 9 may be protected with Q as described above.

Scheme 13

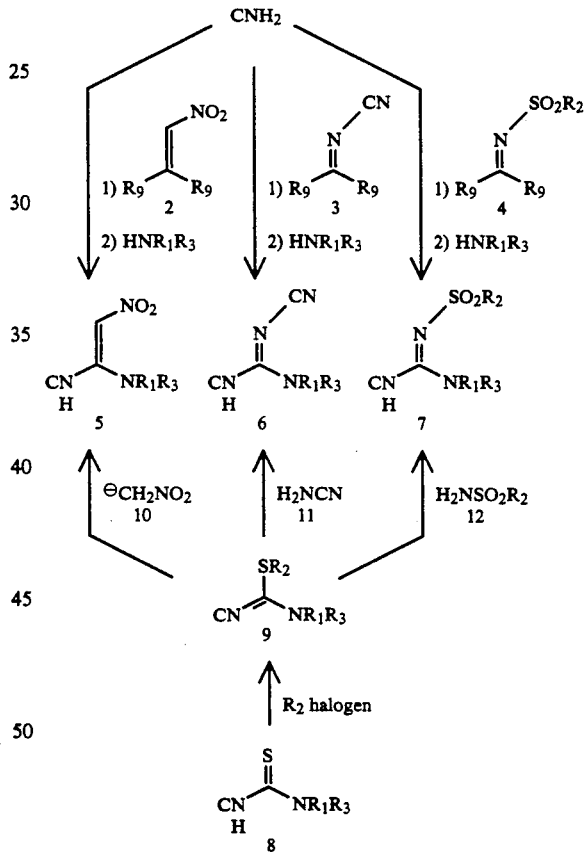

Compounds of formula I, where n=1, may also be prepared by Wittig-type reactions using the aldehyde 1 or 2 of Scheme 14 and phosphorane reagents of type 3 or with phosphonates of type 4 using a suitable base such as potassium or sodium alkoxide in a solvent such as DMSO or THF at −78° to 60° C. A base such as NaH or an alkyl lithium in a solvent such as THF at −78° C. to reflux also may be used.

Alternatively, aldehydes of the type 5 of Scheme 14 (when suitably protected) may be reacted with phosphorane reagents of the type 6 or phosphonates of the type 7, under the conditions described above.

Reagents of the types 3, 4, 6, and 7 may be prepared by standard methods from the corresponding halomethyl derivatives 8 or 9.

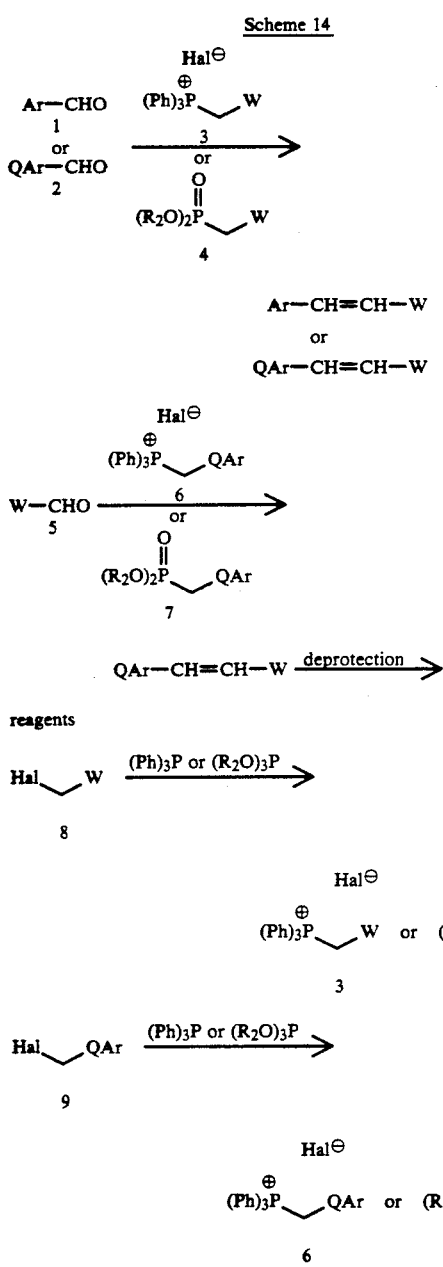

wherein Ar and QAr are as defined above and n=0
Hal=halogen
R₂ and W are as defined above An alternative is a Knoevenagel-type reaction using aldehyde 1 of Scheme 15 with acid derivatives of type 2 or their esters (3) in a solvent such as toluene or pyridine at reflux with a catalyst such as piperidine, piperidine/acetic acid, ammonium chloride, or ammonium acetate. For the esters 3, the intermediate 4 may be isolated, whereupon saponification by standard methods, followed by a decarboxylation using, for example, copper quinoline at 100°–250° C. or diisopropylethylamine in a solvent such as refluxing toluene, xylene, mesitylene, glyme, or diglyme would give the compounds of formula I.

Reagents of type 2 and 3 may be prepared by standard methods, for example, by reaction of the corresponding halomethyl heterocycle 5 with cyanide followed by hydrolysis of the nitrile.

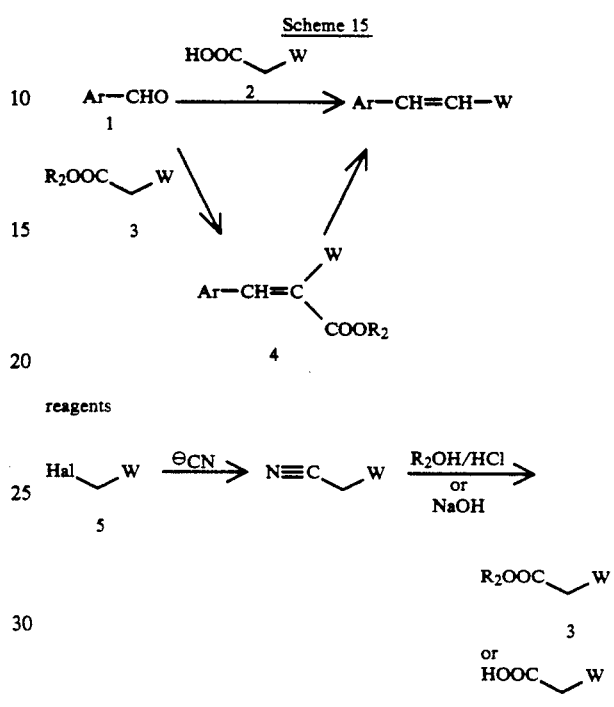

wherein Ar is as defined above and n=0
Hal=halogen
R₂ and W are as defined above Using the Knoevenagel-type reaction, the aldehyde 1 of Scheme 16 and 2-(5-thioxo-4,5-dihydro-1H-1,2,4-triazol-3-yl)acetic acid (prepared by the method described in *Aust. J. Chem.*, 1979, 32, 161–5, N. W. Jacobsen, B. L. McCarthy, and S. Smith) in toluene/pyridine (2:1) is treated with piperidine. The resulting mixture is refluxed to give the styryltriazolethione.

Analogously, the aldehyde 1 of Scheme 16 is converted to the styryltriazolone using 2-(5-oxo-4,5-dihydro-1H-1,2,4-triazole-3-yl)acetic acid (N. W. Jacobsen, B. L. McCarthy, and S. Smith, *Aust. J. Chem.*, 1979, 32, 161–5).

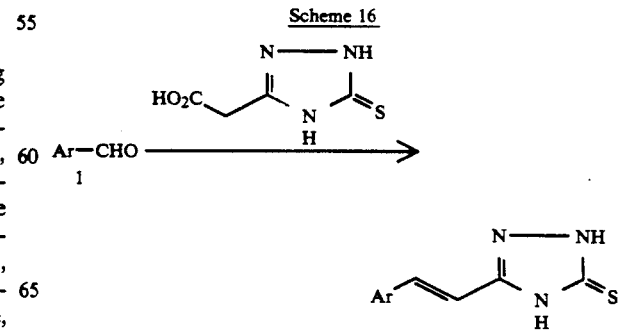

-continued
Scheme 16

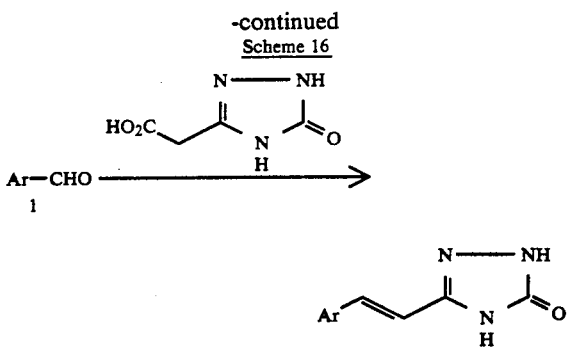

Ar is as defined above wherein n=0.

Alteratively, treatment of the aldehyde 1 of Scheme 17 with a suitably protected methylheterocycle 2 of Scheme 17 (using, for example, an alkyl lithium reagent to form an anion of 2, followed by dehydration using methanolic HCl or toluenesulfonic acid in refluxing toluene) would give compounds of the formula I.

Scheme 17

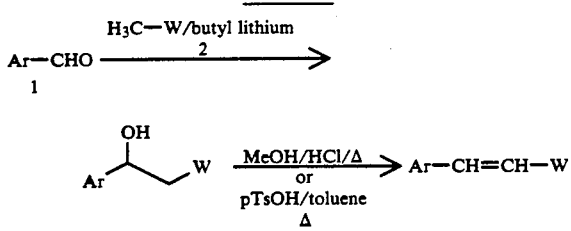

One of skill in the art would recognize variations in the sequence and would recognize variations in the appropriate reaction conditions from the analogous reactions shown or otherwise known which may be appropriately used in the processes above to make the compounds of the Formula I herein. Further, starting materials are known or can be prepared by known methods.

The products of the reactions described herein are isolated by conventional means such as extraction, distillation, chromatography, and the like.

The invention is further elaborated by the representative examples as follows. Such examples are not meant to be limiting.

EXAMPLE 1

3,5-Bis(1,1-dimethylethyl)-4-[(2-methoxyethoxy)-methoxy]benzonitrile

2-Methoxyethoxymethyl chloride (4.1 g, 0.032 mole) is added dropwise to a 0° C. mixture of 3,5-bis(1,1-dimethylethyl)-4-hydroxybenzonitrile (Louis A. Cohen, *Journal of Organic Chemistry* 22, 1333, 1957) (5.0 g, 0.022 mole) and diisopropylaminomethane (4.2 g, 0.032 mole) in methylene chloride (50 ml). The mixture is allowed to warm to room temperature and stir 18 hours. The solution is diluted with methylene chloride (25 ml) and washed with water (25 ml), cold 2M HCl (20 ml), saturated aqueous NaCl, and dried over $MgSO_4$. Filtered and concentrated in vacuo to obtain 6.7 g (6.9 g theor., 97%) of 3,5-bis(1,1-dimethylethyl)-4-(2-methoxyethoxy)methoxy]benzonitrile as a yellow oil.

EXAMPLE 2

3,5-Bis(1,1-dimethylethyl)-4-[[2-methoxyethoxy)methoxy]-benzene carboximidic acid hydrazide 97% anhydrous hydrazine (4.8 g, 0.151 mole) is added dropwise to a stirred 0° C. suspension of sodium hydride (2.8 g of a 60% dispersion in mineral oil, 0.071 mol) in tetrahydrofuran (70 ml) under nitrogen. After 90 minutes, a solution of 3,5-bis(1,1-dimethylethyl)-4-(2-methoxyethoxy)methoxy]benzonitrile (6.7 g, 0.021 mole) in tetrahydrofuran (15 ml) is added dropwise. After stirring two hours at 0° C., water (2.4 ml) is added dropwise. The mixture is poured into cold, saturated aqueous sodium bicarbonate (20 ml). The product is extracted with a 1:1 ethyl acetate/ether mixture (60 ml). The organic layer is washed with saturated aqueous NaCl and dried over $MgSO_4$. Filtration and concentration provided a solid which was recrystallized from ethyl acetate/hexane to give 4.9 g (7.3 g theor., 67%) of 3,5-bis(1,1-dimethylethyl)-4-[(2-methoxyethoxy)methoxy]benzene carboximidic acid hydrazide, mp 133° C.

EXAMPLE 3

5-[3,5-Bis(1,1-dimethylethyl)-4-{2-methoxyethoxy)-methoxyphenyl]-1,3,4-thiadiazole-2(3H)-thione Carbon disulfide (1.6 g, 0.021 mole) is added dropwise to a stirred 0° C. solution of 3,5-bis(1,1-dimethylethyl)-4-[(2-methoxyethoxy)methoxy]benzene carboximidic acid hydrazide (3.0 g, 0.085 mole) in absolute ethanol (36 ml). The mixture is allowed to warm to room temperature and stir three hours. The mixture is stripped of volatiles under reduced pressure and the residue is dissolved in isopropyl ether and the solvent removed under reduced pressure. The resulting solid is recrystallized from isopropyl ether/hexane to give 2.8 g of 5-3,5-bis(1,1-dimethylethyl)-4-(2-methoxyethoxy)methoxy]phenyl]-1,3,4-thiadiazole-2(3H)-thione (3.5 g theor., 80%);

mp 134°–135° C.
Calcd: C, 58.50; H, 7.36; N, 6.82.
Found: C, 58.65, H, 7.51, N, 6.81.

EXAMPLE 4

5-[3,5-Bis(1,1-dimethylethyl -4-hydroxyphenyl]-1,3,4-thiadiazole-2(3H]-thione

Anhydrous zinc bromide (7.3 g, 0.033 mole) is added to a suspension of 5-[3,5-bis(1,1-dimethylethyl)-4-[(2-methoxyethoxy)methoxy]phenyl]-1,3,4-thiadiazole-2(3H)-thione (2.7 g, 0.007 mole) in methylene chloride (10 ml). After 18 hours the mixture is diluted with methylene chloride (50 ml), washed with water (20 ml), saturated aqueous $NaHCO_3$ (20 ml), saturated aqueous NaCl (20 ml), and dried over $MgSO_4$. Filtration and concentration gives a solid which is recrystallized from ethyl acetate/hexane to provide 1.1 g (2.1 g theor., 52%) of 5-[3,5-bis(1,1-dimethylethyl)-4-hydroxyphenyl]-1,3,4-thiadiazole-2(3H)-thione, mp 259.5°–260° C.

Calcd: C, 59.59; H, 6.88; N, 8.69.
Found: C, 59.65; H, 7.00; N, 8.65 .

EXAMPLE 5

1,1-Dimethylethyl 2-3,5-bis(1,1-dimethylethyl)-4-hydroxybenzoyl]hydrazine carboxylic acid Oxalyl chloride (11.4 g, 0.089 mole) is added dropwise to a stirred 0° C. solution of 3,5-bis(1,1-dimethylethyl)-4-hydroxybenzoic acid (15.0 g, 0.059 mole) and 2 drops of dimethy formamide in methylene chloride (200 ml). After 30 minutes the solvent is removed in vacuo. The residue is dissolved in tetrahydrofuran (120 ml) and added dropwise to a stirred 0° C. suspension of 1,1-dimethylethyl hydrazine carboxylic acid in tetrahydrofuran (200 ml). After 30 minutes, the solution is allowed to warm to room temperature and stir 18 hours. The mixture is concentrated in vacuo and the residue filtered through a plug of flash silica gel using a petroleum ether eluent. Concentration and trituration with 1:2 isopropyl ether/hexane yields 12.2 g (14.5 g theor., 84%) of 1,1-dimethylethyl-2-[3,5-bis(1,1-dimethylethyl)-4-hydroxybenzoyl]hydrazine carboxylic acid, mp 196.5° C.

Calcd: C, 65.91; H, 8.85; N, 7.69.
Found: C, 66.05; H, 8.98; N, 7.60.

EXAMPLE 6

3,5-Bis(1,1-dimethylethyl)-4-hydroxybenzoic acid, hydrazide 1,1-Dimethylethyl 2-[3,5-bis(1,1-dimethylethyl)-4-hydroxybenzoyl]hydrazine carboxylic acid (4.0 g, 0.011 mole) in tetrahydrofuran (100 ml) is treated with a mixture of water (12 ml) and concentrated hydrochloric acid (30 ml). The resulting mixture is heated on a steam-bath. After 20 minutes the mixture is stripped of volatiles under reduced pressure. The residue is dissolved in water (100 ml) and treated with 1M NaOH until the solution is slightly basic. The product is extracted into ether (600 ml) and the organic layer is washed with saturated aqueous NaCl and dried over MgSO$_4$. Filtration and concentration provides a solid which is recrystallized from isopropyl ether/hexane to yield 1.9 g (2.9 g theor., 66%) of 3,5-bis(1,1-dimethylethyl)-4-hydroxybenzoic acid, hydrazide, mp 187°-188° C.

Calcd: C, 68.15; H, 9.15; N, 10.59.
Found: C, 68.33; H, 9.28; N, 10.35.

EXAMPLE 7

5-3,5-Bis(1,1-dimethylethyl]-4-hydroxyphenyl]-1,3,4-oxadiazol-2(3H)-one 1 diimidazole (0.8 g, 0.005 mole) is
1,1'-Carbonyl dimidazole (0.8 g, 0.005 mole) is added in one portion to a stirred 0° C. solution of 3,5-bis(1,1-dimethylethyl)-4-hydrox-ybenzoic acid hydrazide (1.0 g, 0.004 mole) and triethylamine (0.6 ml, 0.004 mole) in tetrahydrofuran (12 ml). After 18 hours the mixture is concentrated in vacuo and the residue dissolved in ether. The solution is washed with aqueous 2M HCl, saturated aqueous NaHCO$_3$, saturated aqueous NaCl, and dried over MgSO$_4$. Filtered and concentrated in vacuo to obtain a residue which is purified by flash chromatography using 10% ethyl acetate/hexane eluent. Recrystallize from ethyl acetate/hexane to obtain 0.6 g (1.1 g theor., 55%) 5-[3,5-bis(1,1-dimethylethyl)-4-hydroxyphenyl]-1,3,4-oxadiazol-2(3H)-one, mp 246° C.

Calcd: C, 66.19; H, 7.64; N, 9.65.
Found: C, 66.24; H, 7.64; N, 9.63.

EXAMPLE 8

5-3,5-Bis(1,1-dimethylethyl)-4-hydroxyphenyl]-1,3,4-oxadiazole-2(3H)-thione

Potassium hydroxide (1.1 g, 0.019 mole) is added in one portion to a stirred 0° C. solution of 3,5-bis(1,1-dimethylethyl)-4-hydroxybenzoic acid hydrazide (5.0 g, 0.019 mole) and carbon disulfide (3.4 g, 0.044 mole) in absolute ethanol (60 ml). The resulting mixture is stirred 30 minutes at 0° C. before warming to room temperature and stirring one hour. The solution is then heated to reflux for 2.5 hours. The solvent is removed in vacuo and the residue dissolved in water (100 ml) and washed with ether. The aqueous layer is made acidic with 2M HCl and the product extracted with a 1:1 mixture of ethyl acetate/ether. The organic layer is washed with saturated aqueous NaCl and dried over MgSO$_4$. Filtration and concentration gives a solid which is recrystallized from ethyl acetate/isopropyl ether to give 2.2 g (5.8 g theor., 38%) desired 5-3,5-bis(1,1-dimethylethyl)-4-hydroxyphenyl]-1,3,4-oxadiazole2(3H)-thione, mp 253.5° C.

Calcd: C, 62.72; H, 7.24; N, 9.14.
Found: C, 62.81; H, 7.29; N, 9.01.

EXAMPLE 9

2-[3,5-Bis(1,1-dimethylethyl)-4-hydroxybenzoyl]-hydrazinecarbothioamide

Oxalyl chloride (11.5 g, 0.091 mole) is added dropwise to a stirred 0° C. solution of 3,5-bis(1,1-dimethylethyl)-4-hydroxybenzoic acid (15.0 g, 0.059 mole) in methylene chloride (120 ml) and N,N-dimethylformamide (0.5 ml). After one hour, the solvent is removed in vacuo. The residue is dissolved in tetrahydrofuran (70 ml) and added dropwise to a stirred 0° C. suspension of thiosemicarbazide (10.9 g, 0.120 mole) in tetrahydrofuran (300 ml). After the addition is complete the mixture is allowed to warm to room temperature and stir 18 hours. The mixture is concentrated in vacuo and the residue filtered through a plug of flash silica gel using a 1:1 ethyl acetate/heptane mixture as eluent. Concentration and trituration with 1:1 isopropyl ether/hexane yielded 17.6 g (19.4 g theor., 91%) of 2-3,5-bis(1,1-dimethylethyl)-4-hydroxybenzoyl]hydrazinecarbothioamide, mp 210°-211° C.

Calcd: C, 59.41; H, 7.79; N, 12.99.
Found: C, 59.47; H, 8.08; N, 13.21.

EXAMPLE 10

4-(5-Amino-1,3,4-thiadiazol-2-yl)-2,6-bis(1,1-dimethylethyl)phenol

Methanesulfonic acid (0.94 g, 0.010 mole) is added dropwise to a 0° C. suspension of 2-[3,5-bis(1,1-dimethylethyl-4-hydroxybenzoyl]hydrazinecarbothioamide in toluene (19.5 ml). After the addition is complete the suspension is heated to reflux for four hours. The mixture is cooled to 10° C. and filtered. The filtrate is washed with cold toluene. The solid is suspended in water (20 ml) and treated with concentrated NH$_4$OH. The mixture is filtered, the solid washed with cold water (30 ml), and dried in vacuo to give 0.4 g of 4-(5-amino-1,3,4-thiadiazol2-yl)-2,6-bis(1,1-dimethylethyl)-phenol (1.9 g theor., 20%), mp 261° C.

Calcd (0.1 hydrate): C, 62.55; H, 7.61; N, 13.68.
Found: C, 62.32; H, 7.39; N, 13.40.

EXAMPLE 11

1,1-Dimethylethyl 2-[3-[3,5-bis(1,1-dimethylethyl)-4-hydroxyphenyl]-1-oxo-2-propenyl]hydrazinecarboxylic acid Oxalyl chloride (2.9 g, 0.023 mole) is added dropwise to a stirred 0° C. solution of 3,5-bis(1,1-dimethylethyl)-4-hydroxycinnamic acid (4.3 g, 0.016 mole) in methylene chloride (30 ml) and N,N-dimethylformamide (0.5 ml). After one hour the solvent is removed in vacuo. The residue is dissolved in methylene chloride (30 ml) and added dropwise to a stirred 0° C. solution of 1,1-dimethylethyl hydrazinecarboxylic acid (4.5 g, 0.034 mole). After the addition is complete, the mixture is allowed to warm to room temperature and stir 18 hours. The mixture is concentrated in vacuo and the residue dissolved in methylene chloride (50 ml) and washed with aqueous 2M HCl, saturated aqueous NaCl, and dried MgSO$_4$. Filtration and concentration gives a solid which was recrystallized from ethyl acetate/isopropyl ether to provide 4.6 g (6.1 g theor., 76%) of 1,1-dimethylethyl 2-3-[3,5-bis(1,1-dimethylethyl)-4-hydroxyphenyl]-1-oxo-2-propenyl]hydrazinecarboxylic acid, mp 184° C.

EXAMPLE 12

3,5-Bis(1,1-dimethyethyl)-4-hydroxycinnamic acid hydrazide 1,1-Dimethylethyl 2-[3-[3,5-bis(1,1-dimethylethyl)-4-hydroxyphenyl]-1-oxo-2-propenyl]hydrazinecarboxylic acid (4.3 g, 0.011 mole) in absolute ethanol (20 ml) is treated with aqueous 2M HCl (11.0 ml, 0.022 mole). The resulting mixture is heated on a steam-bath for one hour. The mixture is stripped of volatiles under reduced pressure and the residue partitioned between ether and water. The layers are separated and the aqueous phase is treated with saturated aqueous NaHCO$_3$ until basic. The product is extracted out with a mixture of 1:1 ethyl acetate/ether. The organic extract is washed with saturated aqueous NaCl and dried over MgSO$_4$. Filtration and concentration provides a solid which is triturated in hot hexane and filtered to yield 3.0 g (3.2 g theor., 94%) of 3,5-bis(1,1-dimethylethyl)-4-hydroxycinnamic acid hydrazide, mp 166° C.

EXAMPLE 13

5-2-3,5-Bis(1,1-dimethylethyl]-4-hydroxyphenyl]-ethenyl]-1,3,4-oxadiazole-2(3H)-one Carbonyl diimidazole (0.7 g, 0.004 mole) is added in one portion to a stirred 0° C. solution of 3,5-bis(1,1-dimethylethyl)-4-hydroxy-cinnamic acid hydrazide (1.0 g, 0.003 mole) and triethylamine 0.4 g, 0.004 mole) in tetrahydrofuran (12 ml). The mixture is stirred at 0° C. for 15 minutes and then allowed to warm to room temperature and stir 45 minutes. The solution is concentrated and the residue dissolved in ether (50 ml) and washed with aqueous 2M HCl. The product is extracted from the organic layer by treatment with aqueous 1M NaOH (20 ml). The aqueous extract is made acidic by treatment with cold aqueous 2M HCl and the product is extracted with ether. The organic layer is washed with saturated aqueous NaCl and dried over MgSO$_4$. Filtration and concentration provided a solid which was recrystallized from ethyl acetate/hexane to give 1.0 g (1.1 g theor., 94%) of 5-[2-3,5-bis(1,1-dimethylethyl]-4-hydroxyphenyl]ethenyl]-1,3,4-oxadiazole-2(3H)-one, mp >260° C.

Calcd: C, 68.33; H, 7.65; N, 8.85.
Found: C, 68.32; H, 7.71; N, 8.89.

EXAMPLE 14

(E)-2,4-Dihydro-5-[2-[4-hydroxy-3,5-bis(1,1-dimethylethyl)phenylethenyl]-3H-1,2,4-triazole-3-thione A solution of 2-(5-thioxo-4,5-dihydro-1H-1,2,4-triazol-3-yl)acetic acid (prepared by the method described in *Aust. J. Chem.*, 1979, 32, 161–5, Nowel W. Jacobsen, Bruce L. McCarthy, Stephanie Smith) (3.3 g, 0.021 mole) and 3,5-bis(1,1-dimethylethyl)-4-hydroxybenzaldehyde (4.9 g, 0.021 mole) in a 2:1 mixture of toluene/pyridine (300 ml) is treated with piperidine (0.021 mole). The resulting mixture is stirred at reflux for 48 hours. The mixture is concentrated in vacuo and the residue dissolved in ether, the product is extracted from the organic phase with aqueous 1M NaOH. The combined aqueous layers are made acidic by treatment with aqueous 2M HCl, and the product extracted with a 1:1 mixture of ethyl acetate/ether. The organic layer is washed with saturated aqueous NaCl and dried over MgSO$_4$. Filtration and concentration gives a solid which is triturated in hot isopropyl ether and filtered to provide 2.3 g (6.9 g theor., 33%) of desired (E)-2,4-dihydro-5-[2-[4-hydroxy-3,5-bis(1,1-dimethylethyl)-phenyl]ethenyl]-3H-1,2,4-triazole-3-thione, mp 243° C.

Calcd: C, 65.22, H, 7.60; N, 12.68.
Found: C, 65.26; H, 7.83; N, 12.40.

EXAMPLE 15

5-[3,5-Bis(1,1-dimethylethyl]-4-hydroxyphenyl]-2,4-dihydro-3H-1,2,4-triazol-3-one To a solution of 3,5-bis(1,1-dimethylethyl)-4-hydroxybenzoic acid hydrazine (2.8 g, 10.6 mmol) in ethanol (140 ml) and water (50 ml) is added 1N HCl (16 ml) and sodium cyanate (1.03 g, 16 mmol). The reaction mixture is stirred at room temperature for 30 minutes and at 35° C. for five minutes. The reaction mixture is cooled, evaporated, and partitioned between water (100 ml) and ethyl acetate (100 ml). The organic layer is dried (MgSO$_4$) and evaporated. The crude product is cyclized by refluxing a solution in 1N NaOH (2-3 equiv.) for two hours. It is neutralized with 1N HCl and extracted with ethyl acetate. Pure 5-[3,5-bis(1,1-dimethylethyl)-4-hydroxyphenyl]-2,4-dihydro-3H-1,2,4-triazol-3-one (0.32 g, 10%) is separated from 3,5-di-t-butyl-4-hydrox-ybenzoic acid by flash chromatography (silica, EtOAc), mp 276°-280° C.

Analysis: $C_{16}H_{23}N_3O_2$.
Calcd: C, 66.41; H, 8.01; N, 14.52.
Found: C, 66.31; H, 8.10; N, 14.36.

EXAMPLE 16

5-[3,5-Bis(1,1-dimethylethyl]-4-hydroxyphenyl]-2,4-dihydro-4-methyl-3H-1,2,4-triazol-3-one Methyl isocyanate (1.02 g, 18 mmol) is added dropwise to a solution of the 3,5-bis(1,1-dimethylethyl)-4-hydroxybenzoic acid, hydrazide (2.35 g, 8.9 mmol) in absolute ethanol (100 ml). The reaction mixture is stirred at room temperature, concentrated, and poured into ice water. The precipitate (1.2 g) is collected by filtration and dissolved in two equivalents of 1N NaOH. The reaction mixture is refluxed for three hours, and then is cooled and neutralized. The product is extracted into ethyl acetate. Pure 5-[3,5-bis(1,1-dimethylethyl)-4-hydroxyphenyl]-2,4-dihydro-4-methyl-3H-1,2,4-triazol-3-one (0.8 g, 30%) is obtained by recrystallization from methanol, mp 308°-312° C.

Analysis: $C_{17}H_{25}N_3O_2$.
Calcd: C, 67.30; H, 8.31; N, 13.85.
Found: C, 67.04; H, 8.30; N, 13.67.

EXAMPLE 17

5-2-[3,5-bis(1,1-dimethylethyl)-4-hydroxyphenyl]-ethenyl]-2,4-dihydro-3H-1,2,4-triazol-3-one A solution of 3,5-di-t-butyl-4-hydroxybenzaldehyde (3.5 g, 15 mmol), 2-(5-oxo-4,5-dihydro-1H-1,2,4-triazol-3-yl) acetic acid (N. W. Jacobsen, B. L. McCarthy, and S. Smith, Aust. J. Chem., 32 161-5 (1979]) (2.15 g, 15 mmol), and piperidine (1.3 g, 15 mmol) in pyridine (15 ml) and toluene (45 ml) is heated at reflux (with removal of water) for 40 hours. The reaction mixture is cooled, filtered, and evaporated. The residue is partitioned between ethyl acetate (100 ml) and 1N HCl (400 ml). The organic layer is washed two additional times with 1N HCl (400 ml) and then is dried (MgSO4) and evaporated. The residue crystallized upon addition of hot dichloromethane. Recrystallization from isopropyl ether/ethyl acetate gives 5- 2-[3,5-bis(1,1-dimethylethyl)-4-hydroxyphenyl]ethenyl]-2,4-dihydro-3H-1,2,4-triazol-3-one (2.49 g, 40% , mp 280°-284° C.

Analysis $C_{18}H_{25}N_3O_2$.
Calcd: C, 68.54; H, 7.g9; N, 13.32.
Found: C, 68.50; H, 8.04; N, 13.30.

EXAMPLE 18

5-[3,5-Bis(1,1)-dimethylethyl)-4-[(2-methoxyethoxy)-methoxy]phenyl]-3H-1,2,4-triazole-3-thione 1,1'-Thiocarbonyldiimidazole (0.64 g, 0.0036 mole) is added portionwise to a stirred 0° C. solution of 3,5-bis(1,1-dimethylethyl)-4-[(2-methoxyethoxy)methoxy]-benzene carboximidic acid hydrazide (1.0 g, 0.0028 mole) and triethylamine (0.43 ml, 0.003 mole) in tetrahydrofuran (5.0 ml). After the addition is complete the mixture is heated to reflux for 1.5 hours. The solution is cooled and concentrated in vacuo. The residue is dissolved in ether (20 ml) and the solution washed with aqueous 2M HCl, saturated aqueous NaHCO3, saturated aqueous NaCl, and dried over MgSO4. Filtration and concentration in vacuo gives 0.94 g (1.1 g theor., 86%) product after recrystalization from ethyl acetate/isopropyl ether, mp 187° C.

EXAMPLE 19

5-[3,5-Bis(1,1-dimethylethyl)-4-hydroxyphenyl]-3H-1,2,4-triazole-3-thione

Anhydrous zinc bromide (6.6 g, 0.0292 mole) is added to a suspension of 5-[3,5-bis(1,1-dimethylethyl)-4-[(2-methoxyethoxy)methoxy]phenyl]-3H-1,2,4-triazole-3-thione (2.4 g, 0.0058 mole) in methylene chloride (6.0 ml). After 18 hours the mixture is diluted with methylene chloride (30 ml), washed with water 15 ml), saturated aqueous NaHCO3 (15 ml), saturated aqueous NaCl (10 ml), and dried over MgSO4. Filtration and concentration gives a solid which is recrystallized from ethyl acetate/isopropyl ether to provide 0.8 g (1.8 g theor., 44%) of product, mp >250° C.

EXAMPLE 20

5-2-[3,5-Bis(1,1-dimethylethyl -4-hydroxyphenyl]-ethenyl]-1,3,4-oxadiazole-2(3H)-thione Potassium hydroxide (0.5 g, .0096 mole) is added in one portion to a stirred 0° C. solution of 3,5-bis(1,1-dimethyethyl)-4-hydroxycinnamic acid hydrazide (2.8 g, 0.0096 mole) and carbon disulfide (1.7 g, 0.022 mole) in absolute ethanol (15.0 m). The resulting mixture is stirred 1.5 hours at 0° C. before heating to reflux for four hours. The solution is cooled and the solvent is removed in vacuo. The residue is dissolved in water (50 ml) and washed with ether (20 ml). The aqueous layer is made acidic with aqueous 2M HCl and the product extracted with a 1:1 mixture of ethyl acetate/ether. The combined organic extracts are washed with saturated aqueous NaCl and dried over MgSO4. Filtration and concentration gives a solid which is recrystallized from ethyl acetate/hexane to give 1.4 g (3.2 g theor., 44%) desired product, mp 209.5° C.

Calcd: C, 65.03; H, 7.28; N, 8.43.
Found: C, 65.37; H, 7.66; N, 8.24.

EXAMPLE 21

5-3,5-Bis(1,1-dimethylethyl -4-hydroxyphenyl]-1,3,4-thiadiazole-2(3H)-thione

Step 1.

To a solution of the 3,5-bis(1,1-dimethylethyl)-4-hydroxybenzaldehyde oxime (Louis A. Cohen, J. Org. Chem. 1957, 22, 1333) (0.5 g, 2.0 mmole) in DMF (5.0 ml) cooled to 0° C. is added N-chlorosuccinimide (0.35 g, 2.6 mmole) in small portions over 5 minutes. After the addition is complete the mixture is allowed to stir at 0° C. overnight.

The mixture is diluted with water (5 ml) and extracted with ethyl acetate 2×10 ml). The combined organic layers are diluted with hexane (10 ml) and washed with water (2×10 ml), brine (2×10 ml), and dried (MgSO4). Concentration gives 0.3 g (55%) of desired chlorohydroxamate, mp 138° C.

Step 2.

A solution of the above chlorohydroxamate (0.3 g, 1.1 mmole) in tetrahydrofuran (5 ml) is added dropwise to a 0° C. suspension of anhydrous hydrazine (0.25 g, 7.7 mmole) in tetrahydrofuran (5 ml) slowly over 40 minutes. After the addition is complete the mixture is allowed to stir two hours at 0° C. The solution is poured into ice cold saturated NaHCO3 (5 ml). The aqueous layer was extracted with 1:1 EtOAc/Et2O (2×10 ml). The combined organic layers are washed with brine (10 ml), and dried (MgSO4). Concentration in vacuo gives 0.15 g (49%) of desired hydrazino-hydroxamate after recrystallization (EtOAc/isopropyl ether), mp 172°-175.5° C. (dec.)

Step 3.

To a solution of the hydrazino-hydroxamate (1.2 g, 4.3 mmole) in absolute ethanol (5 ml) cooled to 0° C. is added carbon disulfide (0.71 g, 9.3 mmole) dropwise. The resulting solution is stirred three hours at room temperature. The mixture is concentrated and the residue dissolved in ether (20 ml). The product is extracted with cold 2M NaOH (2×10 ml). The combined aqueous layers are acidified with cold 2M HCl. The product is extracted out with 1:1 EtOAc/Et2O (2×15 ml). The organic extracts are washed with brine (10 ml), and dried (MgSO4). Concentration and recrystallization (EtOH/H₂O) provides 0.8 g (58%) of the desired product after drying in vacuo at 60° C., mp 259°-260° C.

EXAMPLE 22

5-[3,5-Bis(1,1-dimethylethyl)-4-hydroxyphenyl]-1,3,4-thiadiazole-2(3H)-thione, ion(1-), 2-hydroxy-N,N,N-trimethylethanamiom (1:1) salt Choline bicarbonate (46.6% aqueous solution, 0.0763 mole) is added to a warm solution of 5-[3,5-bis(1,1-dimethylethyl)-4-hydroxyphenyl -1,3,4-thiadiazole-2(3H)-thione (25.0 g, 0.0775 mole) in methanol (100 ml). After the addition is complete the mixture is heated to reflux for 1 hour, before cooling and concentrating in vacuo. The residue is crystallized from hot t-butyl-methyl ether, filtered, and dried in vacuo to give 23.9 g (32.9 g theor., 73%) 5-[3,5-bis-(1,1-dimethylethyl)-4-hydroxyphenyl]-1,3,4-thiadiazole-2(3H)-thione,ion(1-), 2-hydroxy-N,N,N-trimethylethanamium (1:1) salt, mp 190°-191° C.

Calcd: C, 59.26; H, 8.29, N, 9.87.
Found: C, 59.27; H, 8.38; N, 9.81.

EXAMPLE 23

5-3,5-Bis(1,1-dimethylethyl)-4-hydroxyphenyl]-1,3,4-thiadiazole-2(3H)-thione, monosodium salt, trihydrate To a slurry of 5-[3,5-bis(1,1-dimethylethyl)-4-hydroxyphenyl]-1,3,4-thiadiazole-2(3H)-thione (52 g, 0.161 mole) in methanol (500 ml) and water (500 ml) is added aqueous 1N NaOH (161 ml, 0.161 mole) at room temperature. After the addition is complete, the solution is allowed to stir at room temperature for ½ hour. The methanol is removed in vacuo and the resulting aqueous mixture lyophilized. The resulting solid hydrated in a closed oven at 20° C. under nitrogen for 48 hours. This provides 63.9 g (64.2 g, theor., 99.5%) of 5-3,5-bis(1,1-dimethylethyl)-4-hydroxyphenyl]-1,3,4-thiadiazole-2(3H)-thione, monosodium salt, trihydrate.

Calcd: C, 48.22; H, 6.83; N, 7.03.
Found: C, 48.48; H, 6.87; N, 6.97.

EXAMPLE 24

5-[3,5-Bis(1,1-dimethylethyl)-4-hydroxyphenyl]-1,3,4-thiadiazole-2(3H)-thione, monosodium salt, pentahydrate To a 0° C. solution of 5-[3,5-bis(1,1-dimethylethyl)-4-hydroxyphenyl]-1,3,4-thiadiazole-2(3H)-thione (5.16 g, 0.0159 mole) in methanol (50 ml), is added aqueous 1.00M NaOH (15.9 ml, 0.0159 mole) dropwise. After the addition is complete the solution is stirred one hour at room temperature before concentrating in vacuo. The residue is slurried in toluene and concentrated. The product is transferred from the flask to a crystallizing dish and dried in vacuo at 80° C. for 48 hours to provide 5.5 g (5.5 g theor., 100%) of 5-3,4-bis(1,1-dimethylethyl)-4-hydroxyphenyl]-1,3,4-thiadiazole-2(3H)-thione, monosodium salt.

Calcd: C, 55.79; H, 6.14; N, 8.13.
Found: C, 55.44; H, 6.18; N, 7.96.

The material is spread out on a crystallizing dish and subjected to an atmosphere of moist air for 48 hours. This provides 6.2 g 6.9 g theor., 90%) of 5-[3,5-bis(1,1-dimethylethyl)-4-hydroxyphenyl]-1,3,4-thiadiazole-2(3H)-thione, monosodium salt, pentahydrate (material melted over large temperature range).

Calcd: C, 44.23; H, 7.19; N, 6.45.
Found: C, 44.18; H, 7.25; N, 6.37.

EXAMPLE 25

5-[3,5-Bis(1,1-dimethylethyl)-4-hydroxyphenyl]-2,4-di hydro-3H-1,2,4-triazole-3-thione Sodium methoxide (2.2 g, 0.041 mole) is added to a solution of 2-3,5-bis(1,1-dimethylethyl)-hydroxybenzoyl]-hydrazinecarbothioamide (4.0 g, 0.0124 mole) in methanol (50 ml). The resulting mixture is stirred at reflux under an atmosphere of nitrogen for 24 hours. The solution is cooled and concentrated in vacuo. The residue is dissolved in water (25 ml) and washed with ether (2×20 ml). The aqueous layer is acidified with cold aqueous 2M HCl (25 ml) and the product extracted out with a 1:1 mixture of ethyl acetate/ether (2×30 ml). The combined organic extracts are washed with saturated aqueous NaCl and dried over MgSO₄. Filtration and concentration gives a residue which is purified by flash chromatography (SiO₂, 30% ethyl acetate/hexane eluent). The solid product is recrystallized from ethyl acetate/hexane to give 2.3 g of 5-[3,5-bis(1,1-dimethylethyl)-4-hydroxyphenyl]-2,4-dihydro-3H-1,2,4-triazole-3-thione. (3.8 g theor., 61%): mp 271° C.

Calcd: C, 62.92; H, 7.59; N, 13.76.
Found: C, 62.80; H, 7.68; N, 13.65.

EXAMPLE 26

5-[3,5-Bis(1,1-dimethylethyl)-4-hydroxyphenyl]-1,3,4,-thiadiazol-2(3H)-one

To a 0° C. solution of 3,5-bis(1,1-dimethylethyl)-4-hydroxy-benzene carbothioic acid, hydrazide (2.0 g, 0.0072 mole) in tetrahydrofuran (10 ml) is added triethylamine (0.39 g, 0.0039 mole) followed by carbonyl diimidazole (0.8 g, 0.0048 mole). The resulting mixture is stirred at 0° C. for one hour. Dilute with ether and extract product with 1M NaOH (2×). The combined aqueous layers are combined and made acidic with aqueous 6M HCl. The product is extracted with 1:1 ether/ethyl acetate. The combined organic extracts are washed with saturated aqueous NaCl and concentration in vacuo provides 1.4 g (2.2 g theor., 64%) of 5-[3,5-bis(1,1-dimethylethyl)-4-hydroxyphenyl]-1,3,4-thiadiazol-2(3H)-one after recrystallization from ethyl acetate/hexane: mp 229° C.

Calcd: C, 62.72; H, 7.24; N, 9.14.
Found: C, 62.81; H, 7.23; N, 9.15.

EXAMPLE 27

N-[5-[3,5-Bis(1,1-dimethylethyl)-4-hydroxyphenyl]-1,3,4-thiadiazole-2-yl]urea

A suspension of 4-(5-amino-1,3,4-thiadiazol2-yl)-2,6-bis(1,1-dimethylethyl)-phenol (1.0 g, 0.0032 mole) in ether (5 ml) is added to a 0° C. solution of N-carbonylsulfamyl chloride (0.46 g, 0.0032 mole) in ether (5 ml). The resulting mixture is stirred 15 minutes before water (10 ml) is added. The mixture is diluted with ether and washed with 2M HCl and saturated aqueous NaCl. Extract with aqueous 1M NaOH (3×). The combined aqueous layers are made acidic with aqueous 2M HCl. The resulting precipitate is filtered an washed with water to provide 0.6 g (1.2 g theor., 53%) of N-[5-[3,5-bis(1,1-dimethylethyl)-4-hydroxyphenyl]-1,3,4-thiadiazole-2-yl]-urea after drying in vacuo at 50° C.; mp >270° C.

Calcd: C, 58.59; H, 6.94; N, 16.08.
Found: C, 58.25; H, 6.93; N, 15.75.

EXAMPLE 28

4-(5-Amino-1,3,4-oxadiazol-2-yl)-2,6-bis(1,1-dimethylethyl)phenol

Cyanogen bromide (0.9 g, 0.0083 mole) is added to a solution of 3,5-bis(1,1-dimethylethyl)-4-hydroxybenzoic acid, hydrazide (2.2 g, 0.0083 mole) and sodium bicarbonate (0.7 g, 0.0083 mole) in dioxane (10 ml)/water (10 ml). The resulting mixture is stirred two hours at room temperature. The solution is concentrated to half volume in vacuo and the residue diluted with water. The resulting solid is filtered and recrystallized from ethyl acetate/hexane to give 1.5 g (2.4 g theor., 58%) of 4-(5-amino-1,3,4-oxadiazol-2-yl)-2,6-bis(1,1-dimethylethyl)phenol after drying in vacuo at room temperature, mp 244°-245° C.

Calcd: C, 66.41; H, 8.01; N, 14.52.
Found: C, 66.31; H, 7.99; N, 14.39.

EXAMPLE 29

(E)-4-2-(5-amino-1,3,4-oxadiazol-2-yl)ethenyl]-2,6-bis(1,1-dimethylethyl)phenol

Cyanogen bromide (0.7 g, 0.0067 mole) is added to a solution of 3,5-bis(1,1-dimethylethyl)-4-hydroxycinnamic acid, hydrazide (1.9 g, 0.0067 mole) and sodium bicarbonate (0.56 g, 0.0067 mole) in dioxane (10 ml)/water (10 ml). The resulting mixture is stirred two hours at room temperature. The solution is concentrated to half volume in vacuo and the residue diluted with water. The resulting solid is filtered and recrystallized from ethyl acetate/hexane to provide 1.1 g (2.1 g theor., 52%) of (E)-4-[2-(5-amino-1,3,4-oxadiazole-2-yl)ethenyl]-2,6-bis(1,1-dimethylethyl)phenol after drying in vacuo at room temperature, mp 221° C.

Calcd: C, 68.54; H, 7.99; N, 13.32.
Found: C, 68.92; H, 7.97; N, 13.28.

EXAMPLE 30

(E)-[3,5-Bis(1,1-dimethylethyl)-4-hydroxyphenyl]-2-propenoic acid, 2-[(methylthio]thioxomethyl]hydrazide Oxalyl chloride (10.3 g, 0.0815 mole) is added dropwise to a stirred 0° C. solution of 3,5-bis(1,1-dimethylethyl)-4-hydroxycinnamic acid (15.0 g, 0.0543 mole) in tetrahydrofuran (50 ml) and N,N-dimethylformamide (0.5 ml). After one hour the solvent is removed in vacuo. The residue is dissolved in tetrahydrofuran 75 ml) and added dropwise to a stirred 0° C. solution of methyl hydrazinecarbodithioate (7.9 g, 0.0652 mole). After the addition is complete, the mixture is allowed to warm to room temperature and stir 18 hours. The mixture is concentrated in vacuo and the residue dissolved in ether (100 ml), and washed with aqueous 0.5M HCl, saturated aqueous NaCl, and dried over MgSO$_4$. Filtration and concentration in vacuo gives a residue which is purified by flash chromatography (SiO$_2$) using 20% ethyl acetate/hexane eluent. Recrystallize from ethyl acetate/hexane to obtain 8.2 g (20.7 g theor., 41 ) of (E)-[3,5-bis(1,1-dimethylethyl)-4-hydroxyphenyl]-2-propenoic acid, 2-[(methylthio)thioxomethyl]hydrazide, mp 200.5° C.

Calcd: C, 59.96; H, 7.42; N, 7.36.
Found: C, 59.94; H, 7.45; N, 7.09.

EXAMPLE 31

(E)-2,6-Bis(1,1-dimethylethyl)-4-[2-[5-(methylthio)-1,3,4-thiadiazol-2-yl]ethenyl]phenol p-Toluenesulfonic acid (1.6 g, 0.0087 mole) is added to a solution of (E)-[3,5-bis(1,1-dimethylethyl)-4-hydroxyphenyl]-2-[(methylthio)thioxomethyl]-propenoic acid, hydrazide (3.3 g, 0.0087 mole) in toluene. After heating at reflux for one hour, the solution is cooled and concentrated. The resulting solid is recrystallized from ethyl acetate/t-butyl-methyl ether to provide 2.1 g (3.2 g theor., 66%) of (E)-2,6-bis(1,1-dimethylethyl)-[2-5-(methylthio)-1,3,4-thiadiazol2-y]ethenyl]phenol, mp 194° C.

Calcd: C, 62.95; H, 7.23; N; 7.73.
Found: C, 63.24; H, 7.42; N, 7.66.

EXAMPLE 32

(E)-2,6-Bis(1,1-dimethylethyl)-4-12-[5-(methylsulfonyl)-1,3,4-thiadiazol-2-yl]ethenyl]-phenol Monoperoxyphthalic acid, magnesium salt hexahydrate (1.4 g of a 80% pure solid, 0.0056 mole) is added portionwise to a 0° C. solution of (E)-2,6-bis(1,1-dimethylethyl)-4-[2-[5-(methylthio)-1,3,4-thiadiazol-2-yl]ethenyl]-phenol (1.0 g, 0.0028 mole) in methanol (15 ml) and water (7 ml). After the addition is complete the solution is allowed to warm to room temperature and stir for two hours. The mixture is then warmed on a steam bath for 45 minutes before cooling and concentrating in vacuo. The residue is dissolved in ether and washed with saturated aqueous NaHCO$_3$, saturated aqueous NaCl, and dried over MgSO$_4$. Filtration and concentration in vacuo gives a residue which is purified by flash chromatography (SiO$_2$) using a 15% ethyl acetate/hexane eluent, followed by recrystallization from ethyl acetate/hexane to give 0.22 g (1.1 g theor., 22%) (E)-2,6-bis(1,1-dimethyl-ethyl)-4-[2-[5-(methylsulfonyl)-1,3,4-thiadiazol2-yl]etheny]phenol, mp 235° C.

Calcd: C, 57.84; H, 6.64; N, 7.09.
Found: C, 57.88; H, 6.77; N, 7.00.

EXAMPLE 33

2,6-Bis(1,1-dimethylethyl)-4-5-(methylthio)-1,3,4-thiadiazol-2-yl]phenol

5-[3,5-Bis(1,1-dimethylethyl) -hydroxyphenyl]-1,3,4-thiadiazole-2(3H)-thione (3.0 g, 0.0093 mole) in tetrahydrofuran (15 ml) is added dropwise to a stirred 0° C. suspension of sodium hydride (0.37 g of a 60% dispersion in mineral oil, 0.0093 moe) in tetrahydrofuran (15 ml) under nitrogen. After 30 minutes, a solution of iodomethane (1.5 g, 0.0102 mole) in tetrahydrofuran (5 ml) is added dropwise. After stirring one hour at 0° C., ether (20 ml) is added and the resulting mixture is washed with aqueous 2M HCl (10 ml), saturated aqueous NaCl, and dried over MgSO$_4$. Filtration and concentration in vacuo, followed by recrystallization from ether/hexane gives 2.6 g of 2,6-bis(1,1-dimethylethyl)-4-[5-(methylthio)-1,3,4-thiadiazol-2-yl]phenol (3.1 g, theor., 83%), mp 122°-122.5° C.

Calcd: C, 60.68: H, 7.19; N, 8.32.
Found: C, 60.73; H, 7.19; N, 8.18.

EXAMPLE 34

[5-[3,5-Bis(1,1-dimethylethyl-4-hydroxyphenyl]-1,3,4-thiadiazol-2-yl]thio]acetic acid Aqueous 1M NaOH (12.4 ml, 0.0124 mole) is added to 0° C. solution of 5-3,5-bis(1,1-dimethylethyl)-4-hydroxyphenyl]-1,3,4-thiadiazole-2(3H)-thione (2.0 g, 0.0062 mole) in methanol (20 ml). This is followed by addition of 2-bromoacetic acid (0.95 g, 0.0068 mole) in one portion. The resulting mixture is allowed to stir four hours with periodic warming. The solution is concentrated in vacuo and the residue is partitioned between ether and water. The layers are separated and the aqueous phase is made acidic with aqueous 6M HCl. The aqueous layer is extracted with 1:1 ethyl acetate/ether (2×). The combined organic layers are washed with saturated aqueous NaCl, and dried over MgSO$_4$. Filtration and concentration in vacuo provides a solid which is recrystallized from ethyl acetate/hexane to give 1.6 g (2.4 g theor., 68%) of [[5-[3,5-bis(1,1-dimethylethyl)-4-hydroxyphenyl]-1,3,4-thiadiazole-2-yl[thio]acetic acid, mp 187.5° C.

Calcd: C, 56.82; H, 6.36; N, 7.36.
Found: C, 56.64; H, 6.23; N, 7.13.

EXAMPLE 35

2,6-Bis(1,1-dimethylethyl)-4-5-(methylsulfinyl)-1,3,4-thiadiazol-2-yl]phenol

30% aqueous hydrogen peroxide (1.7 g, 0.015 mole) is added to a stirred solution of 2,6-bis(1,1-dimethylethyl)-4-[5-(methylthio)-1,3,4-thiadiazol-2-yl]-phenol (5.0 g, 0.015 mole) in glacial acetic acid (20 ml). The resulting mixture is heated to 90° C. for three hours. The mixture is cooled and concentrated in vacuo. The residue is purified by flash chromatography (SiO$_2$, 25% ethyl acetate/hexane eluent) to provide a solid which is recrystallized from ethyl acetate/hexane to give 1.4 g of 2,6-bis(1,1-dimethylethyl)-4-[5-(methylsulfinyl)-1,3,4-thiadiazol-2-yl]-phenol (5.3 g theor., 26%), mp 141.2° C.

Calcd: C, 57.92; H, 6.87; N, 7.95.
Found: C, 58.16; H, 6.97; N, 7.95.

EXAMPLE 36

2,6-Bis(1,1-dimethylethyl)-4-[5-(methylsulfonyl)-1,3,4-thiadiazol-2-yl]phenol m-Chloroperbenzoic acid (3.5 g of a 80-85% pure solid, 0.016-0.017 mole) is added portionwise to a 0° C. solution of 2,6-bis(1,1-dimethylethyl)-4-[5-(methylthio)-1,3,4-thiadiazole-2-yl]-phenol (2.0 g, 0.0059 mole) in dichloromethane (15 ml). After the addition is complete the solution is stirred four hours at 0° C. The mixture is diluted with dichloromethane (20 ml) and the resulting solution is washed with saturated aqueous NaHCO$_3$ (20 ml), saturated aqueous NaCl (10 ml), and dried over MgSO$_4$. Filtration and concentration in vacuo provides a solid which is recrystallized from ethyl acetate/hexane to give 1.6 g of 2,6-bis(1,1-dimethylethyl)-4-5-(methylsulfonyl)-1,3,4-thiadiazol-2-yl]-phenol after drying in vacuo (2.2 g theor., 73%), mp 156.5° C.

Calcd: C, 55.41; H, 6.56; N, 7.60.
Found: C, 55.23; H, 6.53; N, 7.56.

EXAMPLE 37

2,6-Bis(1,1-dimethylethyl)-4-(5-hydrazino-1,3,4-thiadiazol-2-yl)phenol

To a solution of 2,6-bis(1,1-dimethylethyl)-4-[5-(methylsulfonyl)-1,3,4-thiadiazole-2-yl]-phenol (4.1 g, 0.0111 mole) in isopropyl alcohol (30 ml) is added hydrazine (5.0 g, 0.10 mole). The resulting mixture is heated at reflux for four hours. The mixture is cooled and concentrated in vacuo. The residue is dissolved in 1:1 ethyl acetate/ether and washed with saturated aqueous NaCl and dried over MgSO$_4$. Filtration and concentration in vacuo provides a solid which is recrystallized from ethanol/water to give 2.6 g of 2,6-bis(1,1-dimethylethyl)-4-(5-hydrazino1,3,4-thiadiazol-2-yl)phenol after drying in vacuo (3.6 g theor., 73%), mp 109°-122° C.

Calcd: C, 59.97; H, 7.55; N, 17.48.
Found: C, 59.99; H, 7.69; N, 17.45.

EXAMPLE 38

2,6-Bis(1,1-dimethylethyl)-4-5-(methylamino)-1,3,4-thiadiazol-2-ylphenol

To a solution of 2,6-bis(1,1 dimethylethyl)-4-[5-(methylsulfonyl)-1,3,4-thiadiazole-2-yl]phenol (2.0 %, 0.0054 mole) in ethanol (10 ml) is added 25% ethanolic methylamine solution (15 ml), followed by triethylamine (0.6 g, 0.006 mole). The resulting mixture is heated to reflux for three hours. An additional amount of 25% ethanolic methylamine (15 ml) solution is added and the mixture is stirred overnight at reflux. The solution is cooled and the volatiles removed under reduced pressure. The residue is purified by flash chromatography (SiO$_2$) using 30% ethyl acetate/hexane eluent. Recrystallize from ethyl acetate/hexane to obtain 0.8 g (1.7 g theor., 48%) of 2,6-bis(1,1-dimethylethyl)-4-[5-(methylamino)-1,3,4-thiadiazol-2-yl]phenol, mp 207.5°-208° C.

Calcd: C, 68.92; H, 7.89; N, 13.15.
Found: C, 63.67; H, 7.96; N, 13.00.

EXAMPLE 39

N-5-3,5-Bis(1,1-dimethylethyl-4-hydroxyphenyl]-1,3,4-thiadiazole-2-yl]guanidine, monohydrochloride A mixture of sodium tert-butoxide (0.8 g, 0.0082 mole) in tert-butanol (10 ml) is treated with guanidine hydrochloride (0.9 g, 0.0092 mole). The resulting mixture is stirred 30 minutes at room temperature. 2,6-Bis(1,1-dimethylethyl)-4-[5-(methylsulfonyl)-1,3,4-thiadiazole-2-yl]phenol (1.0 g, 0.0027 mole) is then added. The resulting mixture is heated to reflux, stirred overnight, then cooled and concentrated in vacuo. The residue is precipitated from methanol/water and the solid is filtered and washed with water. The solid is dissolved in ether and treated with saturated ethereal HCl. The resulting precipitate is recrystallized from ethanol/ether to give 0.8 g of N-[5-[3,5-bis(1,1-dimethylethyl)-4-hydroxyphenyl]-1,3,5-thiadiazol-2-yl]guanidine, monohydrochloride after drying in vacuo (1.0 g theor., 74% , mp 275.5° C.

Calcd: C, 53.18; H, 6.83; N, 18.24.
Found: C, 52.83; H, 6.84; N, 18.07.

EXAMPLE 40

[5-3,5-Bis(1,1-dimethylethyl]-4-hydroxyphenyl]-1,3,4-thiadiazol-2-yl]cyanamide

To a solution of 2,6-bis(1,1-dimethylethyl)-4-[5-(methylsulfonyl)-1,3,4-thiadiazol-2-yl]phenol (5.0 g, 0.0136 mole) in a mixture of DMF (20 ml) and water (5 ml) is added cyanamide (5.0 g, 0.119 mole) and triethylamine (1.4 g, 0.0136 mole). The mixture is heated to 80° C. and stirred overnight. An additional portion of cyanamide (2.5 g, 0.059 mole) is added and the mixture is stirred six hours at 80° C. The reaction is cooled and partitioned between water and ether. The aqueous layer is acidified with 6M HCl (40 ml). The resulting precipitate is filtered and recrystallized from acetonitrile/water to provide 3.4 g of [5-[3,5-bis(1,1-dimethylethyl)-4-hydroxyphenyl]-1,3,4-thiadiazole-2-yl]cyanamide (4.5 g theor., 76%) after drying in vacuo at 70° C., mp >250° C.

Calcd: C, 61.79; H, 6.71; N, 16.96.
Found: C, 61.93; H, 6.82; N, 16.94.

EXAMPLE 41

2,6-Bis(1,1-dimethylethyl)-4-5-(2-hydroxyethyl)-amino]-1,3,4-thiadiazol-2-yl]phenol To a solution of 2,6-bis(1,1-dimethylethyl)-4-5-(methylsulfonyl)-1,3,4-thiadiazole-2-yl]phenol (4.0 g, 0.0109 mole) in isopropyl alcohol (15 ml) is added ethanolamine (1.9 g, 0.0326 mole). The resulting mixture is heated to reflux for 18 hours. The reaction is cooled and concentrated in vacuo. The resulting solid is recrystallized from methanol/water to give 3.2 g (3.8 g theor., 83%) of 2,6-bis(1,1-dimethyethyl)-4-[5-[(2-hydroxyethyl)-amino]-1,3,4-thiadiazol-2-yl]phenol after drying in vacuo at 65° C., mp 212°-213.5° C.

Calcd: C, 61.86; , 7.79; N, 12.02.
Found: C, 61.74; H, 7.64; N, 11.62.

EXAMPLE 42

5-[3,5-Bis(1,1-dimethylethyl)-4-hydroxyphenyl]-2,4-dihydro-4-methyl-3H-1,2,4-triazole-3-thione Methyl isothiocyanate (4.2 g, 57.1 mmol) is added dropwise to a solution of the 3,5-bis(1,1-dimethylethyl)-4-hydroxybenzoic acid, hydrazide (7.6 g, 28.6 mmol) in 300 ml of absolute ethanol. The reaction mixture is stirred at room temperature for 12 hours, concentrated, and poured onto ice water. The precipitate is collected by filtration and dissolved in 60 ml of 1N NaOH. The reaction mixture is refluxed for three hours, and then is cooled and acidified with 3N HCl. The aqueous mixture is extracted with ethyl acetate (3×). The combined extracts are washed with saturated aqueous NaCl, dried over $Na_2SO_4$, and concentrated in vacuo to give a white solid. Recrystallization from 2-methoxyethanol (100 ml) gives 6.34 g (9.1 g, theor., 70%) of the triazolethione as a white solid, mp >300° C.

Cacld: C, 63.91; H, 7.89; N, 13.15.
Found: C, 63.94; H, 7.80; N, 13.13.

EXAMPLE 43

2,6-Bis(1,1-dimethylethyl)-4-5-(methylthio)-2H-1,2,4-triazol-3-yl]phenol

A solution of 6.00 g (19.64 mmol) of triazolethione (Example 19) and 9.1 g (60.0 mmol) of iodomethane in 50 ml of absolute ethanol is stirred at 50° to 60° C. for 0.5 hour, then cooled to room temperature. The reaction is treated with 300 ml aqueous 0.7 N NaOH, stirred for 30 minutes, and filtered. Recrystallization of the resulting solid from ethanol-water gives 5.26 g (6.27 g theor., 84%) of the S-methylated product as a fluffy, white solid, mp 271°-272° C.

Calcd: C, 63.91; H, 7.89; N, 13.15; S, 10.04.
Found: C, 63.61; H, 7.89; N, 12.96; S, 9.86.

EXAMPLE 44

2,6-Bis(1,1-dimethylethyl)-4-5-(methylsulfinyl)-2H-1,2,4-triazol-3-yl]phenol

A 50° C. solution of 1.0 g (3.13 mmol) of the methylthiotriazole (Example 43) in 50 ml of 95% ethanol is treated dropwise with a solution of 0.92 g (2.98 mmol) of 80% monoperoxyphthalic acid, magnesium salt (MMPP) in 4.5 ml of water over 20 minutes. The resulting reaction mixture is stirred at 40° to 50° C. for two hours and concentrated in vacuo. The residue is dissolved in ethyl acetate, extracted with saturated aqueous $NaHCO_3$ (three times), water and brine, dried over $Na_2SO_4$ and concentrated in vacuo. Flash chromatography ($SiO_2$, 5% methanol-chloroform, 26×6.5 cm) followed by recrystallization from acetone-water gives 0.30 g (1.05 g theor., 29%) of the sulfoxide as a white solid, mp 135°-145° C.

Calcd: C, 60.87; H, 7.51; N, 12.53.
Found: C, 60.51; H, 7.41; N, 12.28.

EXAMPLE 45

2,6-(Bis(1,1-dimethylethyl)-4-3-methylsulfonyl)-1H-1,2,4-triazol-5-yl]phenol

A 50° C. slurry of 2.05 g (6.42 mmol) of the methylthiotriazole (Example 43) in 20 ml of absolute ethanol is treated with 3.9 g (6.3 mmol, 1.96 equiv.) of 80% monoperoxyphthalic acid, magnesium salt (MMPP) in 16 ml of $H_2O$. The reaction is warmed at 50° C. for six hours and cooled to room temperature. The reaction is poured onto cold, saturated aqueous $NaHCO_3$ and filtered, washing with the $NaHCO_3$ solution and water. Recrystallization from ethanol-water gives 1.41 g (2.26 g theor., 62%) of the sulfone as a white solid, mp 286°-287° C.

Calcd: C, 58.10; H, 7.17; N, 11.96.
Found: C, 57.95; H, 7.38; N, 11.99.

EXAMPLE 46

5-[3,5-Bis(1,1-dimethylethyl-4-hydroxyphenyl]-1,3,4-thiadiazole-2-carbonitrile

A solution of 0.52 g (1.41 mmol) of methyl sulfone (Example 36) and 0.15 g (3.06 mmol, 2.17 equiv.) of NaCN in 4 ml dimethylformamide is warmed at 65° C. for 25 hours. An additional portion of NaCN is added and the reaction is warmed at 75° C. for 16 hours and 85° C. for one hour. The reaction is poured onto 3N aqueous HCl and extracted with ethyl acetate (three times). The combined extracts are washed with brine, dried over $Na_2SO_4$, and concentrated in vacuo. Flash chromatography ($SiO_2$, 230-400 mesh, 15×4.5 cm, 15% ethyl acetate-hexane) gives 0.20 g of the nitrile. Recrystallization from cyclohexane gives 0.14 g (0.44 g theor., 31%) of the pure nitrile, mp 140°-140.5° C.

Calcd: C, 64.73; H, 6.71; N, 13.32.
Found: C, 64.99; H, 6.54; N, 13.32.

EXAMPLE 47

2,6-Bis(1,1-dimethylethyl)-4-(1,3,4-thiadiazol-2-yl)-phenol

A solution of 2.00 9 (7.13 mmol) of 3,5-bis(1,1-dimethylethyl)-4-hydroxybenzenecarbothioic acid, hydrazide (preparation is described in Gompper, R., Kutter, E., Schmidt, RR., Liebigs Ann. Chem. 1965, 684, 1374), 1.57 g (10.61 mmol) of triethylorthoformate and 0.07 g (0.37 mmol) of p-toluenesulfonic acid in 30 ml of absolute ethanol is warmed at reflux for six hours, poured onto 200 ml of ice water and filtered. Recrystallization from t-butylmethylether-hexane gives 1.56 g (2.07 g theor., 75%) of the thiadiazole; mp 150°-151° C.

Calcd: C, 66.17; H, 7.64; N, 9.65; S, 11.04.
Found: C, 66.39; H, 7.64; N, 9.53; S, 10.89.

EXAMPLE 48

2,6-Bis(1,1-dimethylethyl)-4-(5-methyl-1,3,4-thiadiazol-2-yl)phenol

A solution of 1.00 g (3.51 mmol) of 3,5-bis(1,1-dimethylethyl)-4-hydroxybenzenecarbothioic acid, hydrazide in triethylorthoacetate (10 ml) containing a catalytic amount of p-toluenesulfonic acid is warmed at 100° C. for 20 h, cooled, and concentrated in vacuo. Chromatography ($SiO_2$, 70-230 mesh, 10×3.5 cm, 50% ethyl acetate-hexane) followed by recrystallization from cyclohexane gives 0.70 g (1.09 g theor., 64%) of the 5-methylthiadiazole as a beige solid, mp 177°-178° C.

Calcd: C, 67.07; H, 7.95; N, 9.20.
Found: C, 67.33; H, 7.96; N, 8.87.

EXAMPLE 49

2,6-(Bis(1,1-dimethylethyl)-4-5-(trifluoromethyl)-1,3,4-thiadiazol-2-yl]phenol

A solution of 2.0 g (7.1 mmol) of 3,5-bis(1,1-dimethylethyl)-4-hydroxybenzenecarbothioic acid, hydrazide in 15 ml of tetrahydrofuran is added dropwise to a 0° C. solution of 2.1 g (18.4 mmol) of trifluoroacetic anhydride in 20 ml of tetrahydrofuran under a nitrogen atmosphere. The reaction is stirred at 0° C. to room temperature over three hours, room temperature for 19 hours, and at reflux for one hour. The cooled reaction mixture is partitioned between 100 ml t-butylmethylether and 150 ml of water. The aqueous layer is extracted with t-butylmethylether (2×50 ml). The combined organic extracts are washed with 5% aqueous $NaHCO_3$ (2×30 ml), 3N aqueous HCl (2×30 ml), and brine (50 ml), dried over $Na_2SO_4$, and concentrated in vacuo to give a foam. Chromatography (flash, $SiO_2$, 70-230 mesh, 25% ethyl acetate-hexane, 13×3.5 cm) followed by recrystallization from isopropanol-water gives 1.03 g (2.54 g theor., 41%) of the title compound, mp 96°-97° C.

Calcd: C, 56.97; H, 5.91; N, 7.82.
Found; C, 57.29; H, 6.31; N, 7.74.

EXAMPLE 50

5-3,5-Bis(1,1-dimethylethyl)-4-hydroxyphenyl]-1,3,4-thiadiazole-2-carboxylic acid, methyl ester A 0° C. solution of 2.8 g (22.8 mmol, 1.10 equiv.) of methylchlorooxalate in 40 ml of tetrahydrofuran is treated with a solution of 5.8 g (20.7 mmol) of 3,5-Bis(1,1-dimethylethyl)-4-hydrox-ybenzenecarbothioic acid, hydrazide (preparation is described in Gomper, R., Kutter, D., Schmidt, RR. (*Liebigs. Ann. Chem.* 1965, 684, 1374) in 40 ml of tetrahydrofuran over 10 minutes. The reaction is stirred at room temperature for 48 hours and concentrated in vacuo. Recrystallization from ethyl acetate-cyclohexane then from cyclohexane (two times) gives 2.98 g (7.21 g theor., 41 ) of the carbomethoxy-thiadiazole as a yellow solid; mp 154°-155° C.

Calcd: C, 62.04; H, 6.94; N, 8.04; S, 9.20.
Found: C, 61.74; H, 6.91; N, 7.86; S, 8.81.

EXAMPLE 51

5-[3,5-bis(1,1-dimethylethyl)-4-hydroxyphenyl]-1,3,4-thiadiazole-2-carboxamide

A solution of 2.0 ml (3.20 mmol) of 1.6M n-butyllithium in hexane is added dropwise to liquid ammonia (3-5 ml) at −78° C. over 10 minutes under a nitrogen atmosphere. The resulting white slurry is treated slowly with 10 ml of tetrahydrofuran and the resulting mixture of lithium amide at −78° C. is treated dropwise with a solution of 1.08 g (3.10 mmol) of 5-3,5-bis(1,1-dimethylethyl)-4-hydroxyphenyl]1,3,4-thiadiazole-2-carboxylic acid, methyl ester in 3 ml of tetrahydrofuran. The reaction is allowed to warm slowly to room temperature and stirred for a total of 18 hours. The reaction is quenched with 100 ml of saturated aqueous $NH_4Cl$ and extracted with t-butylmethylether (3X). The combined organic extracts are washed with brine, dried over $Na_2SO_4$, and concentrated in vacuo to give a yellow solid. Chromatography flash, $SiO_2$, 70-230 mesh, 30% ethyl acetate-hexane) followed by recrystallization from toluene gives 0.68 g (1.03 g theor., 66%) of the desired product as a pale yellow solid, mp 200°-201° C.

Calcd: C, 61.23; H, 6.95; N, 12.60.
Found: C, 61.39; H, 6.93; N, 12.40.

EXAMPLE 52

5-[3,5-Bis(1,1-dimethylethyl]-4-hydroxyphenyl]-1,3,4-thiadiazole-2-carbothioamide A mixture of 1.5 g (4.5 mmol) of 5-3,5-bis(1,1-dimethylethyl)-4-hydroxyphenyl]-1,3,4-thiadiazole-2-carboxamide and 1.0 g (2.2 mmol) of $P_2S_5$ in 20 ml of dioxane is warmed at reflux for one hour under a nitrogen atmosphere. The reaction is poured through a plug of $SiO_2$, washing with t-butylmethylether. Recrystallization from toluene gives 0.45 g (1.6 g theor., 28%) of the thioamide as a yellow solid, mp 215°-216° C.

Calcd: C, 58.42; H, 6.63; N, 12.02.
Found: C, 58.76; H, 6.80; N, 11.73.

EXAMPLE 53

3,5-Bis(1,1-dimethylethyl)-4-[(2-methoxyethoxy)-methoxy]benzoio acid, methyl ester 2-Methoxyethoxymethyl chloride (24.0 q, 192.7 mmol) is added dropwise to a 0° C. mixture of 25.0 g (94.6 mmol) of 3,5-bis(1,1-dimethylethyl)--hydroxybenzoic acid, methyl ester and 27.5 g (212.4 mmol) of diisopropylethylamine in 50 ml of $CH_2Cl_2$ under a nitrogen atmosphere. The reaction is stirred at 25° C. for 24 hours and then poured onto saturated aqueous $NH_4Cl$ and the layers are separated. The aqueous layer is extracted with t-butylmethyl ether (2×150 ml). The combined organic extracts are washed with saturated aqueous $NH_4Cl$, water and brine (2×), dried over $Na_2SO_4$, and concentrated in vacuo to give 33.2 g of the desired product as an orange oil. The product is pure enough to use in subsequent reactions. A sample can be purified by chromatography (flash, $SiO_2$, 230-400 mesh, 29×6.5 cm, 15% t-butylmethylether-hexane) followed by Kugelrohr distillation.

Calcd: C, 68.15; H, 9.15.
Found: C, 67.78; H, 9.09.

EXAMPLE 54

5-[3,5-Bis(1,1-dimethylethyl)-4-[(2-methoxethoxy)-methoxy]phenyl]-1H-1,2,4-triazole-3-amine A 0° C. slurry of 7.00 g (63.32 mmol) of aminoguanidine hydrochloride in 30 ml of methanol is treated with 3.42 g (63.31 mmol) of sodium methoxide. The mixture is treated dropwise with 5.60 g 15.89 mmol) of 3,5-bis(1,1-dimethylethyl)-4-[(2-methoxyethoxy)methoxy]-benzoic acid, methyl ester in 20 ml of methanol over 30 minutes under a nitrogen atmosphere. The reaction is warmed at reflux for 40 hours and poured onto 400 ml of ice water. The aqueous mixture is neutralized to pH 7 using 3N HCl. The precipitate is collected and recrystallized from toluene to give 2.79 g (5.98 g theor., 47%) of the product as a white solid, mp 233°-235° C.

EXAMPLE 55

4(3-Amino-1H-1,2,4-triazol-5-yl)-2,6-bis(1,1-dimethylethyl)phenol

Hydrogen chloride (g) is bubbled for 45 minutes through a slurry of 2.50 g (6.66 mmol) of 5-[3,5-bis(1,1-dimethylethyl)-4-[(2-methoxyethoxy)-methoxy]-phenyl]-1H-1,2,4-triazole-3-amine in 45 ml of methanol immersed in an ice bath. The reaction is exothermic and becomes homogeneous. The reaction is stirred for two hours at room temperature and concentrated in vacuo to give a foam. The residue is armed in 50 ml of t-butyl-methylether and allowed to cool to give a white solid. The solid is dissolved in aqueous 1N NaOH and extracted with t-butylmethylether (2×) and the aqueous layer is neutralized to pH 7 with aqueous 3N HCl. The resulting solid is isolated by filtration and recrystallized from acetonitrile-water to give 0.30 g (1.92 g, theor., 16%) of the aminotriazole as a white solid, mp >250° C.

Calcd: C, 66.64; H, 8.39; N, 19.43.
Found: C, 66.41; H, 8.32; N, 19.17.

EXAMPLE 56

3,5-Bis(1,1-dimethylethyl)-4-[(2-methoxyethoxy)-methoxy oximebenzamide

A mixture of 19.0 g (0.06 mole) of 3,5-bis(1,1-dimethylethyl)-4-[(2-methoxyethoxy)methoxy]benzonitrile and 3.0 g (0.09 mole) of hydroxylamine in absolute ethanol (600 ml) is stirred and heated at 80°-90° C. for 18 hours. The mixture is cooled and ethanol is evaporated leaving a solid residue. Recrystallization from ethyl acetate and hexane affords 27.4 g (62%) of analytically pure 3,5-bis(1,1-dimethylethyl)-4-[(2-methoxyethoxy)methoxy]oximebenzamide, mp 134°-135° C. Analyzed for $C_{19}H_{32}N_2O_4$:

Calcd: C, 64.74; H, 9.15; N, 7.95.
Found: C, 64.73; H, 9 09; N, 7.83.

EXAMPLE 57

3,5-Bis(1,1-dimethylethyl)-N-[(ethoxycarbonyl)oxy]-4-[(2-methoxyethoxy)methoxy]benzenecarboximidamide A solution of 2.5 g (0.007 mole) of 3,5-bis(1,1-dimethylethyl)-4-[(2-methoxyethoxy)methoxy]oximebenzamide and 1.0 g (0.009 mole) of triethylamine in chloroform (15 ml) is treated with 0.8 g (0.007 mole) of ethyl chloroformate over 10 minutes. The solution is stirred at room temperature for one hour, then washed with water (2×20 ml). The organic layer is dried (anhydrous magnesium sulfate) and evaporated to yield a white solid. Recrystallization from chloroform and petroleum ether affords 2.6 g (85%) of analytically pure 3,5-bis(1,1-dimethylethyl)-N-[(ethoxycarbonyl) oxy]-4-[(2-methoxyethoxy)methoxy]-benzenecarboximidamide, mp 115°-117° C.

Analyzed for $C_{22}H_{36}N_2O_6$:
Calcd: C, 62.24; H, 8.55; N, 6.60.
Found: C, 62.50; H, 8.72; N, 6.66.

EXAMPLE 58

3-[3,5-Bis(1,1-dimethylethyl)-4-[(2-methoxyethoxy)-methoxy]phenyl]-1,2,4-oxadiazol-5(4H)-one A solution of 5.0 g (0.012 mole) of 3,5-bis(1,1-dimethylethyl)-N-[(ethoxycarbonyl)oxy]-4-[(2-methoxyethoxy)methoxy]benzenecarboximidamide in toluene (150 ml) is stirred at 120°-130° C. for 18 hours. The toluene is evaporated (vacuum) and the residual oil solidifies upon standing. The solid is recrystallized from ethyl acetate and hexane giving 3.1 g (70%) of analytically pure 3-[3,5-bis(1,1-dimethylethyl)-4-[(2-methoxyethoxy)methoxy]phenyl]-1,2,4-oxadiazol-5(4H)-one, mp 112°-114° C.

Analyzed for $C_{20}H_{30}N_2O_5$:
Calcd: C, 63.46; H, 7.99; N, 7.40.
Found: C, 63.82; H, 8.05; N, 7.33.

EXAMPLE 59

3-[3,5-Bis(1,1-dimethylethyl)-4-hydroxyphenyl1,2,4-oxadiazol-5(4H)-one

A mixture of 1.9 g (0.005 mole) of 3-[3,5-bis(1,1-dimethylethyl)-4-[(2-methoxyethoxy)-methoxy]phenyl]-1,2,4-oxadiazol-5(4H)-one and 5.7 g (0.025 mole) of zinc bromide in dichloromethane (10 ml) is stirred vigorously at room temperature for three hours. The dichloromethane is then carefully decanted and the white solid is washed with additional dichloromethane (2×50 ml). The combined organic layers are washed with 10% sodium bicarbonate (2×50 ml), saturated sodium chloride (2×50 ml) and dried (anhydrous magnesium sulfate). Concentration leaves a solid which is crystallized from ethyl acetate and hexane giving 0.7 g (48% of 3-[3,5-bis(1,1-dimethylethyl)-4-hydroxyphenyl]-1,2,4-oxadiazol-5(4H)-one, mp 189°-191° C.

Analyzed for $C_{16}H_{22}N_2O_3$:
Calcd: C, 66.18; H, 7.64; N, 9.65.
Found: C, 65.84; H, 7.58; N, 9.34.

EXAMPLE 60

3,5-Bis(1,1-dimethylethyl)-4-[(2-methoxyethoxy)-methoxy]-O-acetyloximebenzamide

In a manner analogous to Example 57, 6.0 g (0.017 mole) of 3,5-bis(1,1-dimethylethyl)-4-[(2-methoxyethoxy)methoxy]oximebenzamide is reacted with 1.3 g (0.017 mole) of acetyl chloride to give 4.5 g (68%) of analytically pure 3,5-bis(1,1-dimethylethyl)-4-[(2-methoxyethoxy)methoxy]-O-acetyloximebenzamide, mp 134°-137° C.

Analyzed for $C_{21}H_{34}N_2O_5$:
Calcd: C, 63.93; H, 8.69; N, 7.10.
Found: C, 63.99; H, 8.87; N, 6.91.

EXAMPLE 61

3-[3,5-Bis(1,1-dimethylethyl)-4-[(2-methoxyethoxy)-methoxy]phenyl]-5-methyl-1,2,4-oxadiazole A solution of 4.0 g (0.01 mole) of 3,5-bis(1,1-dimethylethyl)-4-[(2-methoxyethoxy)-methoxy]-O-acetyloximebenzamide in xylene (125 ml) is stirred at 120°–130° C. for 18 hours. The xylene is evaporated (vacuum) and the residual oil solidifies upon standing. The solid is recrystallized from ethyl acetate and hexane giving 3.0 g (81%) of analytically pure 3-[3,5-bis(1,1-dimethylethyl)-4-[(2-methoxyethoxy)methoxy]phenyl]-5-methyl-1,2,4-oxadiazole mp 75°–77° C.

Analyzed for $C_{21}H_{32}N_2O_4$:
Calcd: C, 66.99; H, 8.57; N, 7.44.
Found: C, 67.21; H, 8.39; N, 7.37.

EXAMPLE 62

2,6-Bis(1,1-dimethylethyl)-4-(5-methyl-1,2,4-oxadiazol3-yl)phenol

In a manner analogous to Example 59, 2.6 g (0.007 mole) of 3-3,5-bis(1,1-dimethylethyl)-4-[(2-methoxyethoxy)methoxy]phenyl]-5-methyl-1,2,4-oxadiazole is reacted with 7.7 g (0.03 mole) of zinc bromide to give 0.94 g (48%) of 2,6-bis(1,1-dimethylethyl)-4-(5-methyl-1,2,4-oxadiazol-3-yl)-phenol; mp 126°–127° C.

Analyzed for $C_{17}H_{24}N_2O_2$:
Calcd: C, 70.79; H, 8.39; N, 9.72.
Found: C, 70.78; H, 8.22; N, 9.61.

EXAMPLE 63

4-(5-Amino-1,2,4-oxadiazol-3-yl)-2,6-bis(1,1-dimethylethyl)phenol

To a solution of 2.6 g (0.044 mole) of guanidine in absolute ethanol (100 ml) is added dropwise a solution of 6.2 g (0.022 mole) of 3,5-bis(1,1-dimethylethyl)-N,4-dihydroxybenzenecarboximidoyl chloride in absolute ethanol (60 ml). The mixture is stirred at room temperature for 18 hours, then evaporated to dryness (vacuum). The oil is dissolved in ethyl acetate (125 ml) and poured into water (125 ml). While stirring, the solution is acidified (pH 4.0–5.0) with 1N hydrochloric acid. The organic layer is separated, washed with water (2×100 ml), and dried (anhydrous magnesium sulfate). Evaporation of the organic layer leaves 5.0 g of crude material. Purification by flash chromatography (silica gel, ethyl acetate/hexane elution) gives 1.0 g (16%) of analytically pure 4-(5-amino-1,2,4-oxadiazol-3-yl)-2,6-bis(1,1-dimethylethyl)phenol, mp 202°–204° C.

Analyzed for $C_{16}H_{23}N_3O_2$:
Calcd: C, 66.41; H, 8.01; N, 14.52.
Found: C, 66.56; H, 8.20; N, 14.56.

EXAMPLE 6

5-3,5-Bis(1,1-dimethylethyl)-4-[[2-methoxyethoxy)-methoxyphenyl)-3-bromo-1,2,4-oxadiazole To a vigorously stirred suspension of 9.5 9 (0.030 mole) of 3,5-bis(1,1-dimethylethyl)-4-(2-methoxethoxy methoxy]benzonitrile and 3.9 g (0.050 mole) of sodium bicarbonate in toluene (5.0 ml) heated at 90° C., is added 3.0 g (0.015 mole) of solid dibromoformaldoxime (G. R. Humphrey and S. H. B. Wright, *J Heterocyclic Chem* 26:23 (1989)) in small portions over 20 minutes. After 18 hours at 90° C. the mixture is cooled, diluted with ethyl acetate (40 ml), washed with saturated sodium chloride (2×40 ml), and dried (anhydrous magnesium sulfate). Evaporation of ethyl acetate leaves a brown oil. Purification by flash chromatography (silica gel, ethyl acetate/hexane elution) yields 1.6 g (25%) of analytically pure 5-[3,5-bis(1,1-dimethylethyl)-4-[(2-methoxyethoxy)methoxy]phenyl]-3-bromo-1,2,4-oxadiazole, mp 89°–91° C.

Analyzed for $C_{20}H_{29}BrN_2O_4$:
Calcd: C 54.42; H, 6.62; N, 6.35.
Found: C, 54.73; H, 6.48; N, 6.31.

EXAMPLE 65

4-(3-Bromo-1,2,4-oxadiazol-5-yl)-2,6-bis(1,1-dimethylethyl)phenol

In a manner analogous to Example 59, 0.8 g (0.002 mole) of 5-[3,5-bis(1,1-dimethylethyl)-4-[(2-methoxyethoxy)methoxy]phenyl]-3-bromo-1,2,4-oxadiazole is reacted with 2.0 g (0.009 mole) of zinc bromide to give 0.4 g (65%) of 4-(3-bromo-1,2,4-oxadiazol-5-yl)-2,6-bis(1,1-dimethylethyl)phenol, mp 113°–115° C.

Analyzed for $C_{16}H_{21}BrN_2O_2$:
Calcd: C, 54.39; H, 5.99; N, 7.93.
Found: C, 54.53; H, 6.06; N, 7.88.

EXAMPLE 66

O-[3,5-Bis(1,1-dimethylethyl)-4-hydroxybenzoyl]-oximeacetamide

A mixture of 1.7 g (0.007 mole) of 3,5-di-tertbutyl 4-hydroxybenzoic acid, 0.5 g (0.007 mole) of acetamidoxime (K. P. Flora, B. van't Riet, and G. L. Wampler, *Cancer Research* 38:1291 (1978)) and 0.9 g (0.007 mole) of 1-hydroxy-benzotriazole hydrate (1-HBT) in DMF (35 ml) is cooled in an ice bath. N,N'-dicyclohexylcarbodiimide (1.5 g, 0.007 mole) is added and the mixture is stirred at room temperature for 18 hours. The reaction mixture is poured into ice water (60 ml) and extracted with ethyl acetate (2×30 ml). The layers are separated, and the aqueous phase is made basic with 10% sodium bicarbonate, then extracted with ethyl acetate (50 ml). The organic layers are combined, filtered, and washed successively with 10% sodium bicarbonate (2×50 ml) and water (2×50 ml), then dried over anhydrous magnesium sulfate. Evaporation of solvent leaves a yellow solid. Purification by flash chromatography (silica gel, ethyl acetate/hexane elution) yields 1.3 g (62%) of O-3,5-bis(1,1-dimethylethyl)-4-hydroxybenzoyl]oximeacetamide, mp 175°–176° C.

Analyzed for $C_{17}H_{26}N_2O_3$:
Calcd: C, 66.63; H, 8.55; N, 9.14.
Found: C, 66.59; H, 8.55; N, 9.04.

EXAMPLE 67

2,6-Bis(1,1-dimethylethyl)-4-(3-methyl-1,2,4-oxadiazol-5-yl]phenol

A solution of 4.2 g (0.01 mole) of 0-[3,5-bis(1,1-dimethylethyl)-4-hydroxybenzoyl]oximeacetamide in xylene (125 ml) is stirred at 120°–130° C. for 18 hours. The xylene is evaporated (vacuum) and the residual oil solidifies upon standing. The solid is recrystallized from ethyl acetate and hexane giving 2.4 g (62%) of analytically pure 2,6-bis(1,1-dimethylethyl)-4-(3-methyl-1,2,4-oxadiazol-5-yl)phenol), mp 126°–127° C.

Analyzed for $C_{17}H_{24}N_2O_2$:
Calcd: C, 70.79; H, 8.39; N, 9.72.
Found: C, 70.87; H, 8.34; N, 9.60.

EXAMPLE 68

2-Chloro-0-3,5-bis(1,1-dimethylethyl)-4-hydroxybenzoyl]oximeacetamide

In a manner analogous to Example 66, 13.2 g (0.05 mole) of 3,5-di-tert-butyl-4-hydroxybenzoic acid is reacted with 5.7 g (0.05 mole) of 2-chloroacetamidoxime (Karl P. Flora, Bart van't Riet, and Galen L. Wampler, Cancer Research 38:1291 (1978)) in the presence of 1-HBT (7.1 g, 0.05 mole) and N,N'-dicyclohexylcarbodiimide (12.0 g, 0.06 mole). Evaporation of solvent leaves a solid. Purification by flash chromatography (silica gel, ethyl acetate/hexane elution) yields 12.1 g (67%) of 2-chloro-O-[3,5-bis(1,1-dimethylethyl)-4-hydroxybenzoyl]oximeacetamide, mp 173°–175° C.

Analyzed for $C_{17}H_{25}ClN_2O_3$:
Calcd: C, 59.90; H, 7.39; N, 8.22.
Found: C, 60.00; H, 7.46; N, 8.18.

EXAMPLE 69

4-3-(Chloromethyl)-1,2,4-oxadiazol-5-yl]-2,6-bis-(1,1-dimethylethyl)phenol

A solution of 3.7 g (0.011 mole) of 2-chloro-0-[3,5-bis(1,1-dimethylethyl)-4-hydroxybenzoyl]oximeacetamide in toluene (100 ml) is stirred at 120°–130° C. for 18 hours. The toluene is evaporated (vacuum) and the residual oil solidifies upon standing. The solid is recrystallized from ethyl acetate and hexane giving 2.8 g (80%) of analytically pure 4-3-(chloromethyl)-1,2,4-oxadiazol-5-yl]-2,6-bis(1,1-dimethylethyl)phenol, mp 93°–94° C.

Analyzed for $C_{17}H_{23}ClN_2O_2$:
Calcd: C, 63.25; H, 7.18; N, 8.68.
Found: C, 63.25; H, 7.20; N, 8.66.

EXAMPLE 70

2,6-Bis(1,1-dimethylethyl)-4-[3-(1-pyrrolidinylmethyl)-1,2,4-oxadiazol-5-yl]phenol A mixture of 0.5 g (0.002 mole) of 4-3-(chloromethyl)-1,2,4-oxadiazol-5-yl]-2,6-bis(1,1-dimethylethyl)phenol and 0.4 g (0.006 mole) of pyrrolidine in DMF (10 ml) is stirred at room temperature for three hours. The mixture is poured into ice water (50 ml) and extracted with ethyl acetate (3×25 ml). The organic phase is washed with water (3×40 ml), dried (anhydrous magnesium sulfate), and evaporated, leaving an oil. Purification by flash chromatography (silica gel, ethyl acetate/hexane elution) yields 0.4 g (73%) of analytically pure 2,6-bis(1,1-dimethylethyl)-4-[3-(1-pyrrolidinylmethyl)-1,2,4-oxadiazol5-yl]phenol, mp 100°–102° C.

Analyzed for $C_{21}H_{31}N_3O_2$:
Calcd: C, 70.55; H, 8.74; N, 11.76.
Found: C, 70.71; H, 8.82; N, 11.68.

EXAMPLE 71

4-3-[(Dimethyamino)methyl]-1,2,4-oxadiazol-5-yl]-2,6-bis(1,1-dimethylethyl)phenol In a manner analogous to Example 70, 0.5 g (0.002 mole) of 4-[3-(chloromethyl)-1,2,4-oxadiazol-5-yl]-2,6-bis(1,1-dimethylethyl)phenol is reacted with excess dimethylamine gas to give 0.3 g (59%) of analytically pure 4-[3-[(dimethyamino)methyl]-1,2,4-oxadiazol-5-yl]-2,6-bis(1,1-dimethylethyl)phenol, mp 129°–130° C.

Analyzed for $C_{19}H_{29}N_3O_2$:
Calcd: C, 68.85; H, 8.82; N, 12.68.
Found: C, 68.71; H, 9.01; N, 12.51.

EXAMPLE 72

2,6-Bis(1,1-dimethylethyl)-4-[3-(methylamino)methyl]1,2,4-oxadiazol-5-yl]phenol

In a manner analogous to Example 70, 0.8 g (0.002 mole) of 4-[3-(chloromethyl)-1,2,4-oxadiazol5-yl]-2,6-bis(1,1-dimethylethyl)phenol is reacted with excess monomethylamine gas to give 0.2 g (31%) of analytically pure 2,6-bis(1,1-dimethylethyl)-4-[3-[(methylamino)methyl]-1,2,4-oxadiazol-5-yl]phenol, mp 120°–122° C.

Analyzed for $C_{19}H_{27}N_3O_2$:
Calcd: C, 68.11; H, 8.57; N, 13.24.
Found: C, 68.11; H, 8.88; N, 13.12.

EXAMPLE 73

2,6-Bis(1,1-dimethylethyl)-4-3-(methylthio)methyl-1,2,4-oxadiazol-5-yl]phenol

A mixture of 2.3 g 0.007 mole) of 4-3-(chloromethyl)-1,2,4-oxadiazol-5-yl]-2,6-bis(1,1-dimethylethyl)phenol and 0.7 g (0.009 mole) of sodium thiomethoxide in methanol (90 ml) is heated at 75° C. for 1.5 hours. The solution is concentrated to one-third the volume (~30 ml) and diluted with water (50 ml), acidified (pH 4) with 1N hydrochloric acid and extracted with ethyl acetate 2×50 ml). The organic phase is washed with saturated sodium chloride (2×40 ml), dried (anhydrous magnesium sulfate) and evaporated to give a solid. Recrystallization from ethyl acetate and hexane affords 1.3 g (55%) of analytically pure (2,6-bis(1,1-dimethylethyl)-4-[3-[(methylthio)methyl]-1,2,4-oxadiazol-5-yl]phenol, mp 97°–98° C.

Analyzed for $C_{18}H_{26}N_2O_2S$:
Calcd: C, 64.63; H, 7.84; N, 8.38.
Found: C, 64.78; H, 7.87; N, 8.35.

EXAMPLE 74

2,6-Bis(1,1-dimethylethyl)-4-3-[(methylsulfonyl)methyl-1,2,4-oxadiazol-5-yl]phenol A solution of 1.2 g (0.002 mole) of the hexahydrate magnesium salt of monoperoxyphthalic acid in water (2.0 ml) is added to 0.4 g (0.001 mole) of 2,6-bis(1,1-dimethylethyl)-4-[3-[(methylthio)methyl]-1,2,4-oxadiazol-5-yl]phenol in absolute ethanol (4 ml) (exothermic reaction) and the mixture is stirred at room temperature for 18 hours. The clear solution is concentrated, and the residue dissolved in diethyl ether (50 ml), successively washed with water (30 ml), 10% sodium bicarbonate (30 ml), saturated sodium chloride (2×30 ml), and dried (anhydrous magnesium sulfate). Evaporation of the ether affords a solid. Recrystallization from diethyl ether gives 0.3 g (71%) of analytically pure 2,6-bis(1,1-dimethylethyl)-4-[3-[(methylsulfonyl methyl -1,2,4-oxadiazol-5-yl]-phenol, mp 153°–155° C.

Analyzed for $C_{18}H_{26}N_2O_4S$:
Calcd: C, 58.99; H, 7.15; N, 7.64.
Found: C, 59.16; H, 6.98; N, 7.56.

EXAMPLE 75

2,6-Bis(1,1-dimethylethyl)-4-(3-trichloromethyl-1,2,4-oxadiazol-5-yl)phenol

Solid 3,5-bis(1,1-dimethylethyl)-4-[(2-methoxyethoxy)methoxy]oximebenzamide (6.0 g, 0.02 mole) is slowly added in portions to cold trichloroacetic anhydride (8 ml). Upon completion the mixture is heated at 120° C. for 20 minutes, then poured into ice water (20 ml). The oily precipitate is extracted with diethyl ether (2×10 ml) and separated. The organic layer is washed successively with water (2×10 ml), 10% sodium bicarbonate (2×10 ml), and water 2×20 ml), then dried (anhydrous magnesium sulfate). Evaporation of solvent leaves an oil which is purified by flash chromatography (silica gel, ethyl acetate/ hexane elution) to give 2.0 g (30%) of analytically pure 2,6-Bis(1,1-dimethylethyl)-4-(3-trichloromethyl-1, 2,4-oxadiazol-5-yl)phenol, mp 100°-102° C.

Analyzed for $C_{17}H_{21}Cl_3N_2O_2$:
Calcd: C, 52.12; H, 5.40; N, 7.15.
Found: C, 52.21; H, 5.37; N, 6.96.

EXAMPLE 76

4-(3-Amino-1,2,4-oxadiazol-5-yl)-2,6-bis(1,1-dimethylethyl)phenol

A mixture of 3.8 g (0.014 mole) of N'-cyano-3,5-bis(1,1-dimethylethyl)-4-hydroxybenzenecarboximidamide, 1.0 g (0.014 mole) of hydroxylamine hydrochloride and 4.3 ml (4.2 g, 0.053 mole) of pyridine in 50 ml of absolute ethanol is stirred at reflux (under a nitrogen atmosphere) for 24 hours. The cooled mixture is filtered and evaporated, and the residue is distributed between 250 ml of water and 100 ml of ether. The aqueous layer is extracted several times with fresh ether, and the combined organic layers are washed with brine. The organic layer is dried (anhydrous sodium sulfate) and evaporated. Recrystallization of the residue from ethyl acetate/hexane yields 2.0 g (50% yield) of the analytically pure oxadiazol product, mp 167°-170° C.

Analyzed for $C_{16}H_{23}N_3O_2$:
Calcd: C, 66.41; H, 8.01; N, 14.52.
Found: C, 66.44; H, 8.12; N, 14.78.

EXAMPLE 77

N'-Cyano-3,5-bis(1,1-dimethylethyl)-4-hydroxybenzenecarboximidamide

To a stirred solution of 17.6 g (0.063 mole) of 3,5-bis(1,1-dimethylethyl)-4-hydroxybenzenecarboximidic acid, ethyl ester (E. Müller, A. Rieker, R. Mayer, and K. Scheffler, Ann 645:36 (1961)) in 250 ml of methanol (under a nitrogen atmosphere) is added 3.2 g (0.076 mole) of cyanamide. The mixture is stirred at reflux for 16 hours, cooled, and filtered. The filtrate is evaporated and the residue is digested briefly on the steam bath with 150 ml of 15% ethyl acetate in dichloromethane and refiltered. The final filtrate is condensed to 25 ml and chromatographed over silica gel, using 15% ethyl acetate in dichloromethane followed by 25% ethyl acetate in dichloromethane elution. A yield of 11.3 g (65%) of chromatographed amidine product is obtained. Recrystallization of a sample from ethyl acetate/hexane yields the analytically pure product of mp 192°-194°.

Analyzed for $C_{16}H_{23}N_3O$:
Calcd: C, 70.29; H, 8.48; N, 15.37.
Found C, 70 22: H, 8.56: N, 15.25.

EXAMPLE 78

4-3-(Dimethylamino)-1,2,4-oxadiazol-5-yl]-2,6-bis(1,1 TM dimethylethyl)phenol

To a stirred mixture of 2.0 g (0.0069 mole) of 4-(3-amino-1,2,4-oxadiazol-5-yl)-2,6-bis(1,1-dimethylethyl)phenol and 2.0 g (0.0067 mole) of paraformaldehyde in 45 ml of glacial acetic acid (under a nitrogen atmosphere) is added 2.0 g (0.032 mole) of sodium cyanoborohydride, in portions over ten minutes. The mixture is stirred at room temperature for 24 hours, then cooled in ice and treated cautiously with 250 ml of ice water. Solid sodium carbonate is added until the reaction mixture becomes slightly basic. The mixture is extracted with ethyl acetate (4×100 ml), and the combined organic layers are washed with brine (2×200 ml), dried (anhydrous sodium sulfate), and evaporated. Recrystallization of the residue from aqueous methanol yields 1.0 g (45% yield) of the analytically pure product, mp 135°-138°.

Analyzed for $C_{18}H_{27}N_3O_2$:
Calcd: C, 68.11; H, 8.57; N, 13.24.
Found: C, 67.71; H. 8.31; N. 13.21.

EXAMPLE 79

5-3,5-Bis(1,1-dimethylethyl)-4-hydroxyphenyl]-1,3,4-thiadiazole-2(3H)-thione, magnesium (2:1)(Salt)

A 0° C. solution of 9.90 g (24.84 mmol) of 5-[3,5-bis(1,1-dimethylethyl)-4-hydroxyphenyl]-1,3,4-thiadiazole-2(3H)-thione in 100 ml of absolute ethanol is treated with 2.52 g (12.40 mmol) of $MgCl_2 \cdot 6H_2O$ and is stirred for 5 minutes. The reaction is stirred at room temperature for 4.5 h and concentrated to 50 ml. The resulting solution is poured onto 860 ml of deionized water and fitted to give 6.8 g (8.74 g theor., 78%) of the magnesium salt as the dihydrate after drying at 80° C. for 18 h.

Calcd: C, 54.65; H, 6.59; N, 7.97; S, 18.89; $H_2O$, 5.12.
Found: C, 54.84; H, 6.85; N, 7.99; S, 19.29; $H_2O$, 5.82.

Recrystallization of a sample from toluene gives have a melting point of 243°-246° C.

EXAMPLE 80

5-3,5-bis(1,1-dimethylethyl)-4-hydroxyphenyl]-1,3,4-thiadiazole-2(3H)-thione, calcium (2:1) (salt)

Calcium chloride dihydrate (1.496, 0.0102 mole) is added in one portion to a solution of 5-[3,5-bis(1,1-dimethylethyl)-4-hydroxy-phenyl]-1,3,4-thiadiazole-2(3H)-thione (8.11 g, 0.0204 mole) in tetrahydrofuran (80 ml). The resulting mixture is stirred hours at room temperature before absolute ethanol (80 ml) is added. The mixture is stirred overnight at room temperature. The solution is concentrated in vacuo and the residue dissolved in tetrahydrofuran and the product is precipitated by the addition of water. Filtration and drying at 80° C. in vacuo provides 4.7 g (6.8 g theor., 68%) 5-[3,5-bis(1,1-dimethylethyl)-4-hydroxyphenyl]-1,3,4-thiadiazole-2(3H)-thione calcium (2:1) (salt), mp 212°-231° C., analyzed for 0.31 hydrate.

Calcd: C, 55.37; H, 6.28; N, 8.07.
Found: C, 55.56; H, 6.26; N, 7.95.

EXAMPLE 81

4-Amino-3-[3,5-bis(1,1-dimethylethyl)-4-hydroxy phenyl]-2,4-dihydro-5H-1,2,4-triazole-5-thione To a solution of 4.00 g (0.13 mol) of 2,6-bis(1,1-dimethylethyl)-4-[5-methylthio)-1,3,4-thiadiazol-2-yl]-phenol in 100 ml of ethanol is added 20.64 g (0.41 mol) of hydrazine hydrate. The resulting mixture is warmed at reflux for 4 hours then cooled to room temperature. The reaction is diluted with water and acidified with cold 3N HCl and the precipitate is collected and recrystallized from N,N-dimethylformamide-water to give 2.10 g (4.17 g theor.; 50%) of 4-amino-3-[3,5-bis(1,1-dimethylethyl)-4-hydroxyphenyl]-2,4-dihydro-5H-1,2,4-triazol-5-thione as a white solid: mp 269°-270° C.

Calcd: C, 59.97; H, 7.55; N, 17.48.
Found: C, 60.30; H, 7.43; N, 17.40.

EXAMPLE 82

2,6-Bis(1,1-dimethylethyl)-4-5-methylthio)-1,3,4-oxa diazol-2-yl]phenol

To a 0° C. solution of 17.95 g 0. 59 mol) of 5-[3,5-Bis(1,1-dimethylethyl)-4-hydroxyphenyl]-1,3,4-oxadiazole-2(3H)-thione in methanol (150 ml) is added 59 mol (0.059 mol) of aqueous 1N NaOH over 15 minutes. The reaction is stirred for 15 minutes, then 9.1 g (0.064 mol) of iodomethane is added dropwise. The reaction is stirred for 2 hours at room temperature, concentrated in vacuo and the resulting solid is recrystallized from methanol-water to give 15.01 g 18.91 g theor., 79%) of 2,6-bis(1,1-dimethylethyl)-4-5-methylthio)-1,3,4-oxadiazol-2-yl]phenol: mp 101°-102° C.
Calcd: C, 63.71; H, 7.55; N, 8.74.
Found: C, 63.75; H, 7.56; N, 8.73.

EXAMPLE 83

2,6-Bis[1,1-dimethylethyl)-4-15-methylsulfonyl)-1,3,4-oxadiazol-2-yl]phenol

A mixture of 15.00 g (0.046 mol) of 2,6-bis(1,1-dimethylethyl)-4-[5-methylthio)-1,3,4-oxadiazole-2-yl]-phenol and 24.15 g (0.23 mol) of $NaHCO_3$ in 600 ml of $CH_2Cl_2$ is stirred at room temperature under $N_2$ atmosphere for one hour. m-chloroperbenzoic acid (23.74 g of a 80 to 85% pure solid, 0.11 to 0.12 mol) is added to the 0° C. reaction mixture and is stirred for one hour. The reaction is stirred at 25° C. overnight, then treated with 10.00 g (0.12 mol) of $NaHCO_2$ and 9.6 g 0.44–0.047 mol) of m-chloroperbenzoic acid. The reaction is stirred overnight then washed with aqueous saturated $NaHCO_3$, water and aqueous saturated NaCl, dried over $MgSO_4$ and concentrated in vacuo. Recrystallization from ethylacetate-hexane (1:1) gives 7.89 g (16.21 g, theor., 49%) of 2,6-bis(1,1-dimethylethyl)-4-[5-methylsulfonyl)-1,3,4-oxadiazol-2-ylphenol: mp 162°-163° C.

EXAMPLE 84

N-5-3,5-Bis(1,1-dimethylethyl]-4-hydroxyphenyl]-1,3,4-oxadiazole-2-yl]guanidine, monochloride Sodium (0.68 g, 29.7 mmol) is dissolved in 40 ml of t-butanol under $N_2$ atmosphere. Guanidine hydrochloride (3.31 g, 34.65 mmol) is added to the sodium t-butoxide solution and stirred at room temperature for 0.5 hour. 2,6-Bis(1,1-dimethylethyl)-4-[5-(methylsulfonyl)-1,3,4-oxadiazole-2-yl]-phenol (3.50 g, 9.93 mmol) is added and the reaction is warmed at reflux overnight. The cool reaction mixture is concentrated in vacuo and is recrystallized from methanol-water. The solid is dissolved in diethyl ether and treated with ethereal HCl and the precipitate is collected and recrystallized from ethanol-ether to give 1.53 g (3.29 g theor., 46%) of N-[5-[3,5-bis(1,1-dimethylethyl)-4-hydroxyphenyl]-1,3,4-oxadiazole-2-yl]-guanidine, monochloride as a white solid: mp 223°-224° C.
Calcd: C, 55.50; H, 7.12; N, 19.03.
Found: C, 54.97; H, 7.22; N, 18.96.

EXAMPLE 85

[5-[3,5-Bis(1,1-dimethylethyl)-4-hydroxyphenyl]-1,3,4-oxadiazol-2-yl]cyanamide

To a solution of 3.00 9 (8.51 mmol) of 2,6-bis(1,1-dimethylethyl)-4-[5-methylsulfonyl)-1,3,4-oxadiazol-2-yl]-phenol in 30 ml of N,N-dimethyl formamide and 5 ml of water is added 3.22 g (76.59 mmol) of cyanamide and 0.9 g (8.51 mmol) of triethylamine. The mixture is warmed at 60° C. overnight with stirring under $N_2$ atmosphere. The reaction is cooled and partitioned between water and ether. The layers are separated and the aqueous layer is acidified with aqueous 6N HCl and the resulting precipitate is isolated by filtration. Recrystallization from acetonitrile-water gives 1.42 g (2.68 g theor., 53%) of the [5-[3,5-bis(1,1-dimethylethyl)-4-hydroxyphenyl]-1,3,4-oxadiazol-2-yl]cyanamide as a white solid: mp dec >230° C.
Calcd: C, 64.95; H, 7.05; N, 17.82.
Found C, 64.60; H, 6.83; N, 17.56.

EXAMPLE 86

N-[5-3,5-Bis(1,1-dimethylethyl)-4-hydroxyphenyl]-1,3,4-thiadiazol-2-ylmethanesulfonamide A slurry of 0.52 g (1.7 mmol) of 4-(5-amino1,3,4-thiadiazol-2-yl]-2,6-bis(1,1-dimethylethyl)phenol and 0.26 g (2.58 mmol) of triethylamine in 6 ml of toluene is treated with 0.30 g (2.58 mmol) of methane sulfonylchloride and warmed at 95°-105° C. for 21 hours under Nitrogen atmosphere. The reaction is cooled to room temperature and poured onto cold aqueous 1 N NaOH (100 ml) and extracted with t-butylmethyl ether (3×20 ml). The aqueous layer is acidified with aqueous 1N HCl and filtered to give a yellow solid. Recrystallization from absolute ethanol gives 0.19 g (0.65 g, theor., 29%) of N-5-[3,5-bis(1,1-dimethylethyl)-4-hydroxyphenyl]-1,3,4-thiadiazol-2-yl]methanesulfonamide as a solid: mp 293°-294° C.
Calcd: C, 53.24; H, 6.57; N, 10.96.
Found: C, 53.18; H, 6.65; N, 10.71.

EXAMPLE 87

N-5-[3,5-Bis(1,1-dimethylethyl]-4-hydroxyphenyl]-1,3,4-thiadiazol-2-yl]-acetamide To a 0° C. suspension of 4-(5-amino-1,3,4-thiadiazol-2-yl)-2,6-bis(1,1-dimethylethyl)-phenol (2.4 g, 0.0079 mole) in tetrahydrofuran (30 ml) is added triethylamine (1.1 ml, 0.0079 mol) followed by acetic anhydride (1.1 g, 0.0108 mole) dropwise. After the addition is complete, the mixture is allowed to warm to room temperature and stir one hour. The solution is concentrated in vacuo and the residue resuspended in ether. The product is extracted out with 1M NaOH (2×) and the combined aqueous layers are acidified with 6M HCl. The resulting precipitate is filtered, washed with water, and dried overnight in vacuo at 80° C. to yield 2.0 g (2.7 g theor., 73%) of N-[5-3,5-bis-(1,1-dimethylethyl)-4-hydroxyphenyl]-1,3,4-thiazol-2-yl]-acetamide, mp 326°-328° C.
Calcd: C, 62.22; H, 7.25; N, 12.09.
Found: C, 62.40; H, 7.20; N, 11.76.

EXAMPLE 88

(E)-5-[2-[3,5-Bis(1,1-dimethylethyl]-4-hydroxyphenyl]-ethenyl]-1,3,4-thiadiazole-2(3H)-thione Sodium thiomethoxide (0.5 g, 0.007 mole) is added to a solution of (E)-2,6-bis(1,1-dimethyl ethyl)-4-[2-[5-(methylthio)-1,3,4-thiadiazol-2-yl]-ethenyl]-phenol (1.0 9, 0.0028 mole) in dimethylformamide (10 ml). The resulting mixture is heated to 75° C. for two hours. The solution is cooled and diluted with water (20 ml). The mixture is treated with 1M NaOH (6 ml) and the aqueous solution is washed with ether (2×). The aqueous layer is made acidic by the addition of cold 6M HCl (3 ml)

and the product is then extracted with a 1:1 ethyl acetate/ diethyl ether mixture (2×). The combined organic layers are washed with brine and dried over MgSO4. Filtration and concentration in vacuo, followed by recrystallization from ethyl acetate/hexane gives 0.55 g of (E)-5-[2-3,5-bis(1,1-dimethylethyl)-4-hydroxyphenyl-]ethenyl -1,3,4-thiadiazol-2(3H)-thione. (0.98 g theor., 57%), mp 248°-249° C.

Calcd: C, 62.03; H, 6.94; N, 8.04.
Found: C, 61.95; H, 6.87; N, 7.88.

EXAMPLE 89

Ethyl N-[5-3,5-bis(1,1-dimethylethyl)-4-hydroxy phenyl]-1,2,4-oxadiazol-3-yl]methanimidoate A mixture of 0.87 g (0 03 mole) of 4-(3-amino-1,2,4-oxadiazol-5-yl)-2,6-bis(1,1-dimethylethyl)phenol and 25 ml (22.3 g; 0.15 mole) of anhydrous triethyl orthoformate is stirred at reflux (under a nitrogen atmosphere) for 24 hours. The cooled mixture is evaporated, and the residue is distributed between 75 ml of dichloromethane and 100 ml of saturated aqueous sodium bicarbonate solution. The aqueous layer is extracted several times with fresh dichloromethane, and the combined organic layers are washed with brine. The organic layer is dried (anhydrous sodium sulfate) and evaporated. Recrystallization of the residue from aqueous acetonitrite yields 0.70 g (67% yield) of ethyl N-[5-[3,5-bis(1,1-dimethylethyl)-4-hydroxyphenyl]-1,2,4-oxadiazol-3-y]methanimidoate, mp 159°-161° C.

Analyzed for $C_{19}H_{27}N_3O_3$:
Calcd: C, 66.06; H, 7.88; N, 12.17.
Found: C, 65.90; H, 7.65; N, 12.22.

EXAMPLE 90

3,5-Bis(1,1-dimethylethyl)-4-[(2-methoxyethoxy)-methoxy]benzenecarbothioamide

Into a solution containing 10.0 g (0.03 mole) of 3,5-bis(1,1-dimethylethyl)-4-[(2-methoxyethoxy)methoxy]-benzonitrile, 5.7 ml (0.04 mole) of triethylamine and 14.2 ml (0.18 mole) of pyridine, hydrogen sulfide gas is bubbled over 15 hours. The mixture is poured into ice water (110 ml), and an oily precipitate solidifies upon standing at 0° C. for 15 hours. The solid is thoroughly washed with water and filtered. Recrystallization from ethyl acetate and hexane gives 7.9 g (71%) of analytically pure 3,5-bis(1,1-dimethylethyl)-4-[2-methoxyethoxy)methoxy]benzenecarbothioamide, mp 113°-115° C.

Analyzed for $C_{19}H_{31}NO_3S$:
Calcd: C, 64.55; H, 8.84; N, 3.96.
Found: C, 64.60; H, 8.93; N, 3.80.

EXAMPLE 91

5-3,5-Bis(1,1-dimethylethyl)-4-hydroxyphenyl]-1,2,4-thiadiazol-3-ol

A solution of 3.15 g (0.009 mole) of 3,5-(1-1-dimethylethyl)-4-[(2-methoxyethoxy)methoxyl]benzenecarbothioamide in dry acetone (8 ml) is added in portions to a −20° C. solution of 2.4 g (0.018 mole) of oxalyl chloride in acetone (4 ml). After stirring at −20° C. for two hours, the mixture is concentrated to an orange colored solid. The crude 2-[3,5-bis(1,1-dimethylethyl)-4-hydroxyphenyl)]-4,5-thiazoledione (3.0 g) and azidotrimethylsilane (2.5 ml, 0.019 mole) in xylene (25 ml) are heated at 120° C. for 3.5 hours. Evaporation of solvent leaves a solid which is recrystallized from ethyl acetate and hexane giving 1.2 g (44%) of analytically pure 5-[3,5-bis(1,1-dimethylethyl)-4-hydroxyphenyl]-1,2,4-thiadiazol-3-ol, mp 230°-232° C.

Analyzed for $C_{16}H_{22}N_2O_2S$:
Calcd: C, 62.71; H, 7.24; N, 9.14.
Found: C, 62.46; H, 7.35; N, 8.97.

EXAMPLE 92

Ethyl [[5-3,5-bis(1,1-dimethylethyl)-4-hydroxyphenyl]-1,3,4-thiadiazol-2-yl]amino]thioxomethyl]-carbamate To a suspension of 4-(5-amino-1,3,4-thiadiazole2-yl)-2,6-bis(1,1-dimethylethyl)phenol (1.5 g, 0.005 mole) in tetrahydrofuran (10 ml) is added ethoxycarbonylisothiocyanate (0.64 g, 0.005 mole) dropwise. The resulting mixture is stirred 18 hours at room temperature, before concentrating in vacuo. The residue is recrystallized from ethanol/water to provide 1.7 g (2.2 g theor., 78%) of the title compound after drying in vacuo at 50° C., mp >250° C.

Calcd: C, 55.02; H, 6.46; N, 12.83.
Found: C, 54.97; H, 6.37; N, 12.59.

EXAMPLE 93

N-[5-[3,5-bis(1,1-dimethylethyl]-4-hydroxyphenyl]-1,3,4-thiadiazol-2-yl]thiourea A solution of the carbamate (0.8 g, 0.0018 mole), prepared in Example 92, in diethyl ether (10 ml) is treated with 4M NaOH (7.3 ml, 0.0293 mole). The resulting mixture is heated to reflux for 1.5 hours. The solution is cooled and diluted with water (20 ml). The layers are separated and the aqueous layer is made acidic with 6M HCl (6 ml). The aqueous layer is extracted with 1:1 EtOAc/Et2O (2×) and the combined organic layer is washed with saturated NaCl and dried over (MgSO4). Filtration and concentration in vacuo provides a solid which is recrystallized from methanol/water to give 0.3 g (0.66 g theor., 44%) of the title compound, mp >280° C.

We claim:

1. A compound of the formula (I)

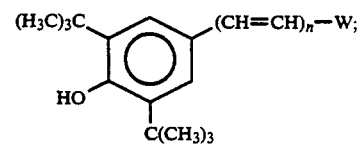

a pharmaceutically acceptable acid addition or base salt thereof or hydrates; wherein n is zero or one, and W is

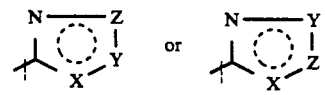

wherein X is O;
Z is N;
Y is (1) C—SR1 wherein R1 is hydrogen or lower alkyl, (2)

wherein R2 is lower alkyl, (3)

wherein $R_2$ is as defined above, (4) C—$NR_3R_3$ wherein $R_1$ is independently as defined above and $R_3$ is hydrogen or lower alkyl, (5) $COR_1$ wherein $R_1$ is independently as defined above, (6) $CR_4$ wherein $R_4$ is halogen, $CF_3$, $CO_2R_1$, or

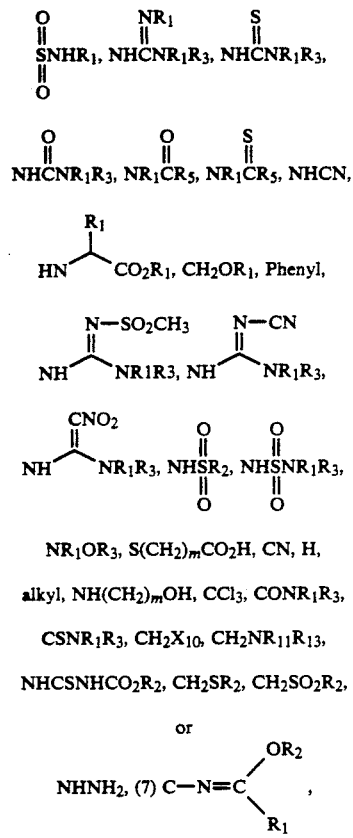

$NR_1OR_3$, $S(CH_2)_mCO_2H$, CN, H, alkyl, $NH(CH_2)_mOH$, $CCl_3$, $CONR_1R_3$, $CSNR_1R_3$, $CH_2X_{10}$, $CH_2NR_{11}R_{13}$, $NHCSNHCO_2R_2$, $CH_2SR_2$, $CH_2SO_2R_2$, or

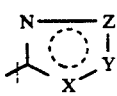

$NHNH_2$, (7) C—N=C wherein m is 1, 2, or 3; $R_{11}$ and $R_{13}$ are hydrogen, lower alkyl or taken together with N form a saturated ring having from 4 to 6 carbons; $X_{10}$ is halogen or $NO_2$; $R_5$ is H, lower alkyl or $OR_1$ and $R_1$, $R_2$, and $R_3$ are independently as defined above; and m is 1, 2, or 3.

2. A compound of claim 1 wherein n is zero.
3. A compound of claim 1 wherein n is one.
4. A compound of claim 2 wherein W is

5. A compound of claim 2 wherein Y is $COR_1$, $CSR_1$,

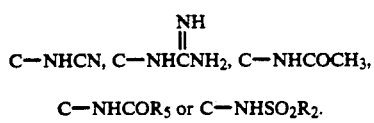

6. A compound of claim 3 wherein Y is $COR_1$, $CSR_1$, $CNR_1R_2$, C—NHCN, C—$\overset{\overset{NH}{\|}}{NHCNH_2}$, C—$NHCOCH_3$, C—$NHCOR_5$, or C—$NHSO_2R_2$.

7. A compound of claim 4 which is 4-(5-amino-1,3,4-oxadiazol-2-yl)-2,6-bis(1,1-dimethylethyl)-phenol.
8. A compound of claim 4 which is 3-[3,5-bis(1,1-dimethylethyl)-4-hydroxyphenyl]-1,2,4-oxadiazol-5(4H)-one.
9. A compound of claim 4 which is 2,6-bis(1,1-dimethylethyl)-4-(5-methyl-1,2,4-oxadiazol-3-yl)phenol.
10. A compound of claim 4 which is 4-(5-amino-1,2,4-oxadiazol-3-yl)-2,6-bis(1,1-dimethylethyl)-phenol.
11. A compound of claim 4 which is 2,6-bis(1,1-dimethylethyl)-4-(3-trichloromethyl-1,2,4-oxadiazol-5-yl)phenol.
12. A compound of claim 2 wherein W is 13. A compound of claim 12 wherein Y is $COR_1$, $CSR_1$, C—NHCN, C—$\overset{\overset{NH}{\|}}{NHCNH_2}$, C—$NHCOCH_3$, C—$NHCOR_5$ or C—$NHSO_2R_2$.

14. A compound of claim 12 which is 4-(3-bromo1,2,4-oxadiazol-5-yl)-2,6-bis(1,1-dimethylethyl)-phenol.
15. A compound of claim 12 which is 2,6-bis(1,1-dimethylethyl)-4-(3-methyl-1,2,4-oxadiazol-5-yl)-phenol.
16. A compound of claim 12 which is 4-[3-(chloromethyl)-1,2,4-oxadiazol-5-yl]-2,6-bis(1,1-dimethylethyl)-phenol.
17. A compound of claim 12 which is 2,6-bis(1,1-dimethylethyl)-4-3-(1-pyrrolidinylmethyl)-1,2,4-oxadiazol-5-yl]phenol.
18. A compound of claim 12 which is 4-[3-[(dimethyamino)methyl]-1,2,4-oxadiazol-5-yl]-2,6-bis(1,1-dimethylethyl)phenol.
19. A compound of claim 12 which is 2,6-bis(1,1-dimethylethyl)-4-3-(methylamino)methyl]-1,2,4-oxadiazol-5-yl]phenol.
20. A compound of claim 12 which is 2,6-bis(1,1-dimethylethyl)-4-3-(methylthio)methyl]-1,2,4-oxadiazol-5-yl]phenol.
21. A compound of claim 12 which is 2,6-bis(1,1-dimethylethyl)-4-[3-[(methylsulfonyl)methyl]-1,2,4-oxadiazol-5-yl]phenol.
22. A compound of claim 12 which is 4-(3-amino-1,2,4-oxadiazol-5-yl)-2,6-bis(1,1-dimethylethyl)phenol.
23. A compound of claim 12 which is 4-[3-(dimethylamino-1,2,4-oxadiazol-5-yl]-2,6-bis(1,1-dimethylethyl)phenol.
24. A compound of claim 3 wherein W is

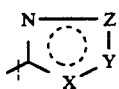

25. A compound of claim 24 which is (E)-4-[2-(5-amino1,3,4-oxadiazol-2-yl)-ethenyl]-2,6-bis(1,1-dimethylethyl)phenol.

26. A compound of claim 3 wherein W is

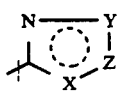

27. A compound of claim 4 which is 5-[3,5-bis(1,1-dimethylethyl)-4-hydroxyphenyl]-1,3,4-oxadiazol-2(3H)-one.

28. A compound of claim 4 which is 5-[3,5-bis(1,1-dimethylethyl)-4-hydroxyphenyl]-1,3,4-oxadiazol-2(3H)-thione.

29. A compound of claim 24 which is 5-[2-[3,5-bis(1,1-dimethylethyl)-4-hydroxyphenyl]ethenyl]-1,3,4-oxadiazole-2(3H)-one.

30. A compound of claim 24 which is 5-[2-[3,5-bis(1,1-dimethylethyl)-4-hydroxyphenyl]ethenyl-1,3,4-oxadiazol-2(3H)-one.

31. A compound of claim 4 which is 2,6-bis(1,1-dimethylethyl)-4-[5-methylthio)-1,3,4-oxadiazol-2-yl]phenol.

32. A compound of claim 4 which is 2,6-bis(1,1-dimethylethyl)-4-[5-methylsulfonyl)-1,3,4-oxadiazol-2-yl]phenol.

33. A compound of claim 4 which is N,[5-[3,5-bis(1,1-dimethylethyl)-4-hydroxyphenyl]-1,3,4-oxadiazole-2-yl]quanidine, monochloride.

34. A compound of claim 4 which is [5-[3,5-bis(1,1-dimethylethyl)-4-hydroxyphenyl]-1,3,4-oxadiazol-2-yl]cyanamide.

35. A compound of claim 4 which is ethyl N-[5-[3,5-bis(1,1-dimethylethyl)-4-hydroxyphenyl]-1,2,4-oxadiazol-3-yl]methanimidoate.

36. A pharmaceutical composition for use as an antiinflammatory agent comprising an antiinflammatory amount of the compound of claim 1 and a pharmaceutical carrier.

37. A method of treating inflammation in a mammal suffering therefrom which comprises administering the compound of claim 1 in unit dosage form.

38. A pharmaceutical composition as claimed in claim 1 additionally comprising an effective amount of a second active ingredient that is a nonsteroidal antiinflammatory drug; a peripheral analgesic agent; a cyclooxygeanse inhibitor; a leukotriene antagonist; an antihistamine agent; a prostaglandin antagonist or a thromboxane antagonist.

* * * * *

UNITED STATES PATENT AND TRADEMARK OFFICE
CERTIFICATE OF CORRECTION

PATENT NO. : 5,256,680
DATED : Oct. 26, 1993
INVENTOR(S) : Connor et al

Page 1 of 2

It is certified that error appears in the above-indentified patent and that said Letters Patent is hereby corrected as shown below:

Column 57, line 7, "C-$NR_3R_3$" should read "C-$NR_1R_3$".

Column 58, line 39, "bromo1,2,4-" should read "bromo-1,2,4-".

Column 58, line 48, "-4-3-(1-" should read "-4-[3-(1-".

Column 58, line 54, "-4-3-(methylthio)" should read "-4-[3-(methylthio)".

Column 58, line 57, "-4-3-(methylthio)" should read "-4-[3-[(methylthio)".

Column 59, line 8, "amino1,3,4-oxadiazol-2-yl)-ethenyl" should read "amino-1,3,4-oxadiazol-2-yl)ethenyl".

Column 59, line 22, "-oxadiazol-" should read "-oxadiazole-".

Column 59, line 29, "oxadiazol-2(3H)-one" should read "oxadiazole-2(3H)-thione".

Column 60, line 6, "N,[5-" should read "N-[5-".

Column 60, line 8, "yl]quanidine," should read "yl]guanidine,".

UNITED STATES PATENT AND TRADEMARK OFFICE
CERTIFICATE OF CORRECTION

PATENT NO.   : 5,256,680
DATED        : Oct. 26, 1993
INVENTOR(S)  : Connor et al It is certified that error appears in the above-indentified patent and that said Letters Patent is hereby corrected as shown below:

Column 60, line 26, "ygeanse" should read "ygenase".

Column 60, line 27, "mine" should read "minic".

Signed and Sealed this

Twenty-fourth Day of May, 1994

Attest:

BRUCE LEHMAN

*Attesting Officer*      *Commissioner of Patents and Trademarks*